United States Patent [19]
Hoffmann et al.

[11] Patent Number: 5,990,278
[45] Date of Patent: Nov. 23, 1999

[54] PROTECTIVE OR ANCHOR GROUPS AND THEIR USE

[76] Inventors: Stefen Hoffmann; Ronald Frank, both of Mascheroder Weg 1, D-38124 Braunschweig, Germany

[21] Appl. No.: 08/793,714

[22] PCT Filed: Sep. 4, 1995

[86] PCT No.: PCT/EP95/03469

§ 371 Date: Mar. 3, 1997

§ 102(e) Date: Mar. 3, 1997

[87] PCT Pub. No.: WO96/07672

PCT Pub. Date: Mar. 14, 1996

[30] Foreign Application Priority Data

Sep. 2, 1994 [DE] Germany .............................. 44 31 317

[51] Int. Cl.⁶ .............................. A61K 38/02; C07K 1/00
[52] U.S. Cl. .......................... 530/333; 530/331; 530/334; 530/335; 530/336; 530/345; 564/133; 564/138; 564/188; 564/192
[58] Field of Search ..................................... 530/331, 333, 530/334, 335, 336, 345; 504/133, 138, 188, 192

[56] References Cited

U.S. PATENT DOCUMENTS

| | | | |
|---|---|---|---|
| 4,454,065 | 6/1984 | Gilvarg et al. | 260/112.5 |
| 4,922,015 | 5/1990 | Breipohl et al. | 562/451 |

FOREIGN PATENT DOCUMENTS 5097789  4/1993  Japan .

OTHER PUBLICATIONS

Masao Kawai et al, Preparation of Protected α–Methoxyglycine and its Incorporation into Peptide Synthesis, Chemistry Letters, pp. 557–580, 1990.

A.R. Brown et al., Solid Phase Synthesis of α–Hydroxyglycine Extended Peptides–Biological Precursors of Peptede Amides, Tetrahedron Letters, vol. 35, No. 5, pp. 789–792, 1994.

N. Nichifor et al, Synthesis of Peptide Derivatives of 5–Fluorouracil, Tetrahedron, vol. 50, No. 12, pp. 3747–3760, 1994.

Kahns & Bundgaard Pharm Res. vol. 8 No. 12 1991 pp. 1533–1538.

JAPIO AN. 93–097789/CAPLUS AN. 1993: 603855/WPIDS AN 93–164426 of JP 05097789.

*Primary Examiner*—Bennett Celsa
*Attorney, Agent, or Firm*—Brooks & Kushman P.C.

[57] ABSTRACT

The invention relates to a carbamide of the general formula $$R_1-CO-NH-C(R_2)(R_3)-X-Y$$

which is protected by a temporary protective group and wherein $R_1$—CO means a carbonyl residue which can be provided as a unit for the chain of a peptide, and can have one or a plurality of amino acid residues;

R2 and R3 mean resides of the carbamide which do not participate in their function, whereby R2 and R3 can be identical or different, but are different when one of the two residues means a hydrogen atom;

X means an oxygen atom or a sulphur atom, and

Y means a protective group for X.

The invention further relates to a process for producing the protected carbamide and to utilisation of the protected carbamide.

The protected carbamide according to the invention can also be linked to a carrier material.

26 Claims, No Drawings

PROTECTIVE OR ANCHOR GROUPS AND THEIR USE

TECHNOLOGICAL FIELD

The present invention pertains to protective and anchor groups useful in peptide synthesis, particularly in multistep peptide synthesis.

BACKGROUND OF THE INVENTION

Regioselective chemical conversion of a compound with a plurality of different chemical functions requires the protection of all these functions as far as that/those by means of which the chemical reaction is to be initiated. Molecule groups (protective groups) are introduced in order to protect these functions. In conjunction with this, these can be removed in a non-disruptive manner and selectively, with re-formation of the original function. For complex multistage syntheses, particularly of natural substances, such as oligopeptides and oligonucleotides, various types of protective groups are necessary. They are characterised by intensely differing conditions of splitting. A system of protective groups in which the individual types are so selectively splittable that all the other respective groups remain unaffected, it termed orthogonal. The principle is the subject of the chemistry of protective groups (see Protective Groups in Organic Synthesis, Greene, T. W. & Wuts, P. G. M. Eds., $2^{nd}$ ed., 1991, John Wiley & Sons Inc., New York).

If the type of protective group has a further reactive function, it can be linked covalently and in a stable way with a carrier material for solid-phase synthesis. Then the terms "active group" or "linker group" are used (see e.g. Breitpohl et al. In *Tetrahedron Lett.* 28 (1987) 5651–5654 and Guibé et al. in *Tetrahedron Lett.* 30 (1989) 2641–2644). A special type of protective group or also active group is that which must firstly be brought into a labile form by a preceding chemical reaction, and which then in a second step can be split off under very gently conditions (protected protective group—"Safety-Catch" grouping; cf. E.g. Patek in *Int. J. Peptide Protein Res.* 42 (1993) 97–1176). Although in such a case two reaction steps are required for splitting, such groupings can have great advantages.

(i) it can be very stable against many, even extremely drastic reaction conditions, but can be split by the sequence of two specific extremely mild reaction steps.

(ii) the labile intermediate stage of the protective group can be sufficiently stable to offer good, or better, opportunities for isolation and cleaning the end product.

SUMMARY OF THE INVENTION

The object underlying the invention is to propose for a carbamide function ($CONH_2$-function) a special type of protective or anchor group having the following features:

(i) the protective or active group is to be protected;
(ii) the labile intermediate stage is to be stable under appropriate reaction conditions and permit cleaning of the intermediate products;

(iii) the labile intermediate stage is to be able to decompose in aqueous physiological buffer solution at neutral pH (7) or almost neutral pH (5 to 9), and re-form the original carbamide function, so that the synthesis product can be used directly (without further cleaning) with a free carbamide function in a biocellular or biochemical test experiment.

According to the invention, there is also to be provided, for a carbamide function ($CO-NH_2$-function), a special type of protective group as an active group for the solid-phase synthesis of peptides (but also other molecular structures with a carbamide function), particularly according to the Fmoc-tBu-method (Fmoc SPPS) (see Fields & Noble in *Int. J. Peptide Protein Res.* 35 (1990) 161–214)and Boc/Bzl method (Boc SPPS) (see Barany et al. Int. J. Peptide Protein Res.(1987) 705–739.

The object underlying the invention is now achieved by a carbamide of the general formula:

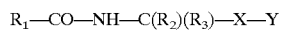

$$R_1-CO-NH-C(R_2)(R_3)-X-Y$$

which is protected by a temporary protective group and wherein $R_1$—CO means a carbonyl residue which can be provided as a unit for the chain of a peptide, and can have one or a plurality of amino acid residues;

R2 and R3 mean resides of the carbamide which do not participate in their function, whereby R2 and R3 can be identical or different, but are different when one of the two residues means a hydrogen atom;

X means an oxygen atom or a sulphur atom, and

Y means a protective group for X.

DETAILED DESCRIPTION OF THE INVENTION

The chemical bond between protective group and carbamide function can thus be a N-acyl-N.O— or N-acyl-N.S acetal structure. This N-acyl-N.O— or N-acyl-N.S acetal can be introduced by conversion of the carboxyl function with the amino function of a suitable N.O— or N.S-acetal, the oxygen or sulphur function being protected and the amino function being free (reaction path A, see illustration). It can further be introduced by conversion of the carbamide function with a suitable keto- or aldehyde function (reaction path B, see illustration). In order that the labile N.O or N>S-acetal (II) can be isolated with a free hydroxyl or thiol function, the N.O or N.S acetal must be flanked by intensely electron-attractive substituents. N.O or N.S acetals with free hydroxyl or thiol function are more or less easily split hydrolytically in an aqueous solution with catalysis of bases. The hydroxyl or thiol function of the protective group is therefore to be protected by a further protective group Y, which prevents hydrolysis of the N.O or N.S acetal under the conditions of synthesis on $R_1$. The Y group is to be stable under the conditions of synthesis on $R_1$.

Principle

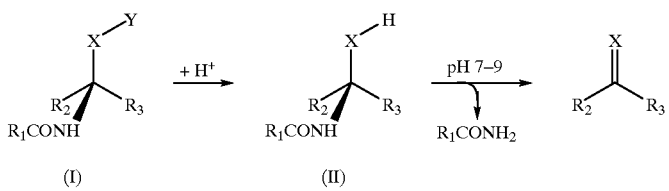

Introduction of the Protective Group

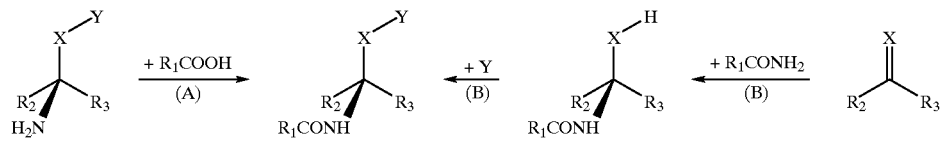

In the above illustration of the general principle of the protective or active group, and of the concept of synthesis, the following can mean:

| | |
|---|---|
| $R_1$ | residue of the compound to be protected; |
| $R_2, R_3$ | residues of the protective group which do not participate in their function; if $R_2$ and $R_3$ have an additional reactive function for a link with carrier materials, for example COOH,$NH_2$SH, then the protective group is used as an active group; |
| Y | the protective group for hydroxyl or thiol function. |

In the carbamide according to the invention, therefore, $R_2$ and/or $R_3$ can be intensely electron-attractive groups, particularly groups according to the Erlenmeyer Rule for O.O, N.O and N.S acetals.

Further, in the carbamide according to the invention, $R_2$ and/or $R_3$ can mean a halogen alkyl group, for example a trifluoromethyl group, or a carboxyl group, if necessary derivatised, for example a —CO—NH—$CH_2$—$CH_2$—COOH group (—CO βAla-OH group), or an alkyl ester carbonyl group, for example a —$COOCH_3$ group.

In the carbamide according to the invention $R_2$ and/or $R_3$ can have an additional reactive function for linking with a carrier material, for example a carboxyl, amino or thiol group.

For Y, reference may be made to Greene & Wuts loc. Cit. In the carbamide according to the invention carbamide can be an alkyl group, for example a methyl, ethyl, i-propyl, t-butyl group, a substituted alkyl group, for example $CH_3$—O—$CH_2$ or $(CH_3)_3$Si—$CH_2$—$CH_2$—O—CH2 group, an aryl group or an alkyl silyl group, e.g. a t-butyldimethylsilyl group.

The object underlying the invention is further achieved by a process for producing a protected carbamide, which is characterised in that a compound with the formula $$H_2N—C(R_2)(R_3)X—Y$$

is converted with a compound of the formula $$R_1—COOH$$

R1, $R_2$ and $R_3$, X and Y having the meanings given above. The object underlying the invention is further achieved by a process for producing a protected carbamide which is characterised in that
 a) a compound of the formula $C(R_2)(R_3)$=X is converted with a compound of the formula $R_1$—CO—$NH_2$ to form a compound with the formula $R_1$—CO—NH—$C(R_2)(R_3)$—XH, and
 b) the XH group of the reaction product according to (a) is transferred into an X—Y group, whereby $R_1, R_2, R_3$, X and Y have the meanings given above.

The carbamide according to the invention can be used for peptide synthesis and for peptide synthesis on a carrier material.

The carbamide according to the invention can also already be linked to a carrier material.

The invention will be explained in more detail in the following by means of examples.

Experimental Part (General Methods)

The following analytical/spectroscopis apparatus was used.

$^1$HNMR/$^{13}$C-NMR: Bruker Model AM-300 und WM-400 with tetrametylsilane (TMS) as internal standard.— $^{19}$F-NMR: $H_3PO_4$ as external standard.

Signal multiplicity: s=singlet, d=doublet, t=triplet, q=quartet, $^nJ_{H,H}$=magnetic couplingng over n bonds between adjacent protons. If signals of diastereomeric mixtures are registered separately from one another, this is indicated by an elevated [dia].— FAB-MS: Kratos MS 50 TC RF with neutral xenon beam(8–9 kV) und Finnigan Mat, Mass Spectrometer 8430 with 3-nitrobenzylalkohol as matrix. The samples were presented in DMSO.— MALDI-TOF: Shimadzu Kratos Analytical Kompact MALDI 111 mit sinapic acid as matrix.— UV/VIS: Carl Zeiss Model PMQ 11 in quartz vessels with 10 mm optical length. ε(dibenzofulvene-piperidine-adduct/MeOH)=5570. RP-$C_{18}$-HPLC: Analyt. HPLC: Pharmacia/LKB Pump P 3500, Liquid Chromatography Controller LCC 500 Plus or LKB 2249 Gradient Pump, LKB 2141 Variable Wavelength Monitor, three-channel flatbed-writer on MacheryNagel Nucleosil 300-7 $C_{18}$ 250×4.— The staged synthesis of peptides is effected according to the usual methods of solid-phase peptide synthesis [Fields, G. B. and Noble, R. L., Int. J. Peptide Protein Res. 35, 161–214 (1990)]. O-chlorotrityl resins (Novabiochem) are charged according to the processes described in the literature, and the protected peptides split off from the-resin as there described (Barlos, K; Chatzi, O.; Gatos, D. und Stavropoulos, G.; lnt. J. Peptide Protein Res., 35 161 (1990). Anchor blocks are identified by (AB) and model compounds with (MV). Compound codes: ([P] protective group or [L] linker group according to path [A] or[B].[Example].[Number]).

Experimental Part (Explanation with reference to Examples)

Protective group for N$^\alpha$-fmoc/tBu-solid-phase peptide synthesis

SYNTHESIS PATH A/EXAMPLE 1

2-(9-Fmoc-amido)-2-methoxy-1.1.1.3.3.3-hexafluoropropane (PA.1.1)$^{(MV)}$
Structure

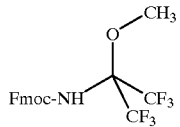

SYNTHESIS PATH 2-(9-Fmoc-amido)-2-hydroxy-1.1.1.3.3.3-hexafluoropropane (PA.1.2)
Empirical Formula (C$_{18}$H$_{13}$F$_6$NO$_3$)

120 mg (50 10$^{-5}$ mol) aminoformic acid-9-fluorenylmethylester are dissolved in a saturated solution of anhydrous hexafluoracetone (caution: toxic) (produces by slow instillation of hexafluoracetone in a mixture of concentrated sulphuric acid and phosphorus pentoxide), in 5 ml THF and stirred for 5 hours at RT. The reaction mixture is concentrated, resuspended in 10 ml diethyl ether, filtered and again concentrated.— Yield: 192 mg (95% of. Th.) (white solid matter).— $^1$H-NMR (400 MHz, CDCl$_3$): δ=7.81 (d, 2H, fluorenyl-H$^1$, $^3$j$_{H.H}$=7.30 Hz), 7.67 (d, 2H, fluorenyl-H$^4$, $^3$J$_{H.H}$,,=7.26 Hz), 7.4 (t, 2H, fluorenylH$^2$,$^3$ J$_{H.H}$=7.30 Hz), 7.25 (t, 2H, fluorenyl-H$^3$,$^3$J$_{H.H}$=7.30), 5.62 (s (br.), 1H, NH), 4.6 (d, 2H, CH—CH$_2$), $^3$j$_{H.H}$=6.67 Hz), 4.23 (t, 1 H, CH—CH$_2$, $^3$j$_{H.H}$=6.67 Hz).— $^{13}$C-NMR (75 MHz, CDCl$_3$): δ=156.4 (s, NH—COO), 142.8 (s, fluorenyl-C$_6$), 141.4 (s, fluorenyl-C$_5$), 128.2 (d, fluorenyl-C$_1$), 127.3 (d, fluorenyl-C$_4$), 124.7 (d, fluorenyl-C$_3$),122.8 (s, CF$_3$),120.3 (d, fluorenyl-H$_2$), 119.0 (s, NH—COH), 68.1 (t, CH—CH$_2$), 46.8 (d, CH—CH$_2$).— $^{19}$F-NMR (376 MHz, CDCl$_3$): δ=-82.2 (s, CF$_3$).— MS (FAB, 3-NBA): m/z=419 (15, [M+H]$^⊕$).

2-(9-Fmoc-amido)-2-methoxy-1.1.1.3.3.3-hexafluoropropane (PA.1.1)
Empirical Formula (C$_{19}$H$_{15}$F$_6$NO$_3$)

101 mg (25 10$^{-5}$ mol) (PA.1.2) are dissolved in 4 ml absolute methanol und 50 μl conc. Sulphuric acid is added. It is stirred for 12 h at RT and the reaction mixture is poured into a saturated NaHCO$_3$ solution. The organic phase is separated, extracted 3× with saturated NaCl and dried over MgSO$_4$. The organic phase is concentrated and crystallised among petroleum benzine.— Yield: 192 mg (95% of Th.) (white solid matter).— $^1$H-NMR (400 MHz, CDCl$_3$): δ=7.81 (d, 2H, fluorenyl-H$^1$, $^3$J$_{H.H}$=7.30 Hz), 7.67 (d, 2H, fluorenyl-H$^4$, $^3$J$_{H.H}$=7.26 Hz), 7.4 (t, 2H, fluorenyl-H$^2$, $^3$J$_{H.H}$=7.30 Hz), 7.25 (t, 2H, fluorenyl-H$^3$, $^3$j$_{H.H}$=7.30), 5.62 (s (br.), 1H, NH), 4.6 (d, 2H, CH—CH$_2$), $^3$J$_{H.H}$=6.67 Hz), 4.23 (t, 1H, CH—CH$_2$, $^3$J$_{H.H}$=6.67 Hz), 1.55 (s, 3H, CH$_3$).— $^{13}$C-NMR (75 MHz, CDCl$_3$): δ=156.4 (s, NH—COO), 142.8 (s, fluorenyl-C$_6$), 141.4 (s, fluorenyl-C$_5$), 128.2 (d, fluorenyl-C$_1$), 127.3 (d, fluorenyl-C$_4$), 124.7 (d, fluorenyl-C$_3$), 122.8 (s, CF$_3$), 120.3 (d, fluorenyl-H$_2$), 119.0 (s, NH—COH), 68.1 (t, CH—CH$_2$), 46.8 (d, CH—CH$_2$), 54.4 (q, CH$_3$).— $^{19}$F-NMR (376 MHz, CDCl$_3$):δ=-82.2 (s, CF$_3$).— MS (FAB, 3-NBA): m/z=419 (15, [M+H]$^⊕$).

Application (PA.1.1) is deprotected with 95% TFA/2.5% TIBS/2.5% water and the reaction product is chromatographically isolated. The deprotected product is hydrolised with buffer system (a) 30% ethanol at RT aminoformic acid-9-fluorylene ester. Hydrolysis is effected within 15 min.

SYNTHESIS PATH B/EXAMPLE 2

2-(N$^\alpha$Ac-Phe-NH)-2-methoxy-1.1.1.3.3.3-hexafluoropropane (PB.2.1)$^{(MV)}$
Structure

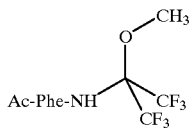

R$_1$: Ac-Phe—
R$_2$: CF$_3$
R$_3$: CF$_3$
X: O
Y: CH$_3$

SYNTHESIS PATH 2-(N$^\alpha$-Ac-Phe-NH)-2-hydroxy-1.1.1.3.3.3-hexafluoropropane (PB.2.2)
Empirical Formula (C$_{14}$H$_{14}$F$_6$N$_2$O$_3$)

103.1 mg (50 10$^{-5}$ mol) N$^\alpha$-acetyl-phenylalanylamide are converted similarly to (PA.1.2). The reaction mixture is concentrated and crystallised among petroleum benzine.— Yield: 182 mg (98% of th.) (white solid matter).— $^1$H-NMR (300 mhz, CDCl$_3$): δ=9.95 (s, 1H, NH), 8.60(s, 1H,OH), 7.3–7.05 (m, 5H,phenyl-H), 6.15 (d, 1H, CONH, $^3$J$_{H.H}$=7.9 Hz),4.97 (AB-q, 1H, CH—NH, $^3$J$_{H.H}$=7.9 Hz, $^3$J$_{H.H}$=6.7 Hz) 3.12 (AB-q,1H, CH$_2$—C$_6$, H$_5$, $^3$J$_{H.H}$=6.7 Hz, $^2$J$_{H.H}$14.0 Hz), 3.12 (AB-q, 1 H, CH$_2$—C$_6$H$_5$, $^3$J$_{H.H}$=6.7 Hz, $^2$J$_{H.H}$=14.0 Hz), 1.92 (s, 3H, CH$_3$).— $^{13}$C-NMR (75 MHz, CDCL$_3$): δ=177.5 (s, CH$_3$ CO), 170.5(s, CO—NH), 135.1 (s, phenyl-H), 129.2 (d, phenyl-H), 128.9 (d, phenyl-H), 127.5 (d, phenyl-H), 127.5 (s, phenyl-H), 120.5 (q, CF$_3$ $^3$J$_{H.H}$=270 Hz), 83.9 (m, NH—COH), 68.1 (t, CH—CH$_2$), 54.7 (d, NH—CH), 37.8 (t,CH$_2$—C$_6$H$_5$), 22.6 (q, CH$_3$).— $^{19}$F-NMR (376 MHz, CDCl$_3$): δ=-82.1 (s, CF$_3$).— MS (FAB, 3-NBA): m/z=373 (15, [M+H]$^⊕$).

2-(Nc$^\alpha$-Ac-Phe-NH)-α-methoxy-1.1.1.3.3.3-hexafluoropropane (PB.2.1)
Empirical Formula (C$_{15}$H$_{16}$F$_6$NO$_3$)

93.1 mg (25 10-5 mol) (PA.2.2) are converted in methanol, similarly to (PA.1.2).— Yield: 192 mg (95% of Th.) (white solid matter in petroleum benzine).— $^1$H-NMR (300 MHz, CDCl$_3$): α=8.95 (s, 1H, NH), 8.60 (s,1H, OH), 7.3–7.05 (m, 5H, phenyl-H), 6.15 (d, 1H, CONH, $^3$J$_{H.H}$=7.9 Hz), 4.97 (AB-q, 1 H, CH—NH, $^3$J$_{H.H}$=7.9 Hz, $^3$J$_{H.H}$=6.7 Hz), 3.12 (AB-q, 1 H, CH$_2$—C$_6$H$_5$), $^3$J$_{H.H}$=6.7 Hz, $^2$J$_{H.H}$=14.0 Hz),1.92 (s, 3H, CH$_3$), 1.55 (s, 3H, CH$_3$).— $^{13}$C-NMR (75 MHz, CDCl$_3$): δ=177.2 (s, CH3—CO), 171.5 (s, CO—NH), 135.1 (s, phenyl-H), 129.2 (d, phenyl-H), 128.9 (d, phenyl-H), 127.5 (d, phenyl-H), 127.5 (s,phenyl-H), 120.5 (q, CF$_3$, $^3$J$_{H.H}$=270 Hz), 83.9 (m, NH—COH), 68.1 (t, CHCH$_2$), 54.7 (d, NH—CH), 54.4 (q, CH$_3$), 37.8 (t, CH$_2$—C$_6$H$_5$), 22.6 (q, CH$_3$)—$^{19}$F-NMR (376 MHz, CDCl$_3$): δ=-82.1 (s, CF$_3$).— MS (FAB, 3-NBA): m/z=388 (11, [M+H]$^⊕$).

Application (PB.2.1) is deprotected with 95% TFA/2.5% TIBS.2.5% water and the reaction mixture is chromatographically isolated. The deprotected product is hydrolysed with buffer system (a) at RT and und 50° C. to form Nα-acetyl-phenylalanylamide. Hydrolysis is effected at RT within 15 min., and at 50° C. within 5 min.

SYNTHESIS PATH B/EXAMPLE 3
2-(N$^\alpha$-9-Fmoc-Asn-OMe)-2-(MeO)-1.1.1.3.3.3-hexafluorpropane (PB.3.1)$^{(MV)}$
Structure

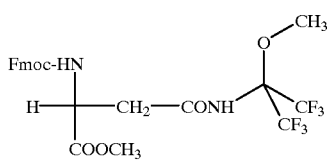

R$_1$: Fmoc-Asn-OH
R$_2$: CF$_3$
R$_3$: CF$_3$
X: O
Y: CH$_3$

SYNTHESIS PATH
2-(N$^\alpha$-9-Fmoc-Asp-β-amido)-2-hydroxy-1.1.1.3.3.3-hexafluoropropane (PB.3.2)
Empirical Formula (C$_{14}$H$_{14}$F$_6$N$_2$O$_3$)
103.1 mg (50 10-5 mol) Nα-9-Fmoc-asparagine are converted similarly to (PA.1.2). The reaction mixture is concentrated and crystallised in petroleum benzine.— Yield: 182 mg (98% of Th.) (white solid matter).— $^1$H-NMR (300 MHz, CDCl$_3$): δ=7.81(d, 2H, fluorenyl-H$^1$, $^3$J$_{H,H}$=7.30 Hz), 7.67 (d, 2H, fluorenyl-H$^4$,$^3$J$_{H,H}$=7.26 Hz), 7.4 (t, 2H, fluorenyl-H$^2$, $^3$J$_{H,H}$=7.30 Hz), 7.25 (t, 2H, fluorenyl-H$^3$, $^3$J$_{H,H}$=7.30), 6.05 (d, 1 H, NH), 4.61 (s(br), 1 H, NHC H—CO), 4.23 (m, 3H, CH—CH$_2$/CH—CH$_2$).— $^{13}$C-NMR (100 MHz, CDCl$_3$): δ=172.8 (s, COOH), 168.5 (s, CO—NH), 156.0 (s, NH—COO), 142.8 (s, fluorenylC$_6$), 141.4 (s, fluorenyl-C$_5$), 128.2 (d, fluorenyl-C$_1$), 127.3 (d, fluorenyl-C$_4$), 124.7 (d, fluorenyl-C$_3$), 122.8 (s, CF$_3$), 120.3 (d, fluorenyl-H$_2$), 119.0 (s, NH—COH), 77.2 (d, NH—CH—CO), 68.1 (t, CH—CH$_2$), 46.8 (d, CH—CH2), 38.8 (t, CH$_2$—CO).— $^{19}$F-NMR (376 MHz, CDCl$_3$): δ=-81.8 (s, CF$_3$).— MS (FAB, 3-NBA) m/z=521 (15, [M+H]$^\oplus$).
2- (N$^\alpha$9-Fmoc-Asn-OMe)-2-(methoxy)-1.1.1.3.3.3-hexafluoropropane (PB.3.1)$^{(MV)}$
Empirical Formula (C$_{15}$H$_{16}$F$_6$NO$_3$)
93.1 mg (25 10$^{-5}$ mol) (PB.3.1) are copnverted in methanol similarly to (PA.1.3).— Ausbeute:192 mg (95% of Th.) (white solid matter in petroleum benzine).— $^1$H-NMR (300 MHz, CDCl$_3$): δ=7.81 (d, 2H, fluorenyl-H$^1$, $^3$J$_{H,H}$=7.30 Hz), 7.67 (d, 2H, fluorenyl-H$^4$, $^3$J$_{H,H}$=7.26 Hz), 7.4 (t, 2H, fluorenyl-H$^3$, $^3$J$_{H,H}$=7.30 Hz), 7.25 (t, 2H, fluorenyl-H$^3$, J$_{H,H}$=7.30), 6.05 (d, 1 H, NH), 4.61 (s(br), 1 H, NH—C H—CO), 4.23 (m, 3H, CH—CH$_2$/CH—CH$_2$), 3.86 (s, 3H, COOCH$_3$), 3.42(s, 3H, CH$_3$O).— $^{13}$C-NMR (100 MHz, CDCl$_3$): δ=172.8 (s, COOH), 168.5 (s, CO—NH), 156.0 (s, NH—COO), 142.8 (s, fluorenyl-C$_6$), 141.4 (s, fluorenyl-C$_5$), 128.2 (d, fluorenyl-C$_1$), 127.3 (d, fluorenyl-C$_4$), 124.7 (d, fluorenyl-C$_3$), 122.8 (s, CF$_3$), 120.3 (d, fluorenyl-H$_2$), 119.0 (s, NH—COH), 77.2 (d, NH—CH—CO), 68.1 (t, CH—C H2), 54.4 (q, CH$_3$), 52.6 (q,COOCH3), 46.8 (d, CH—CH$_2$), 38.8 (t, CH$_2$—CO).— $^{19}$F-NMR (376 MHz, CDCl$_3$):β=-81.8 (s, CF$_3$ ).— MS (FAB, 3-NBA): m/z=551 (15, [M+H]$^\oplus$).

Application
(PA.3.1) dislays total stability against 20% piperidin/DMF over 3 h at RT. (PA.3.1) is deprotected with 95% TFA/2.5% TIBS/2.5% water and the reaction product is chromatographically isolated. The deprotected product is hydrolysed with buffer system (a)/40% ethanol at RT to form Fmoc-asparagine methyl ester. Hydrolysis is effected at RT within 15 min. The hydrolysis takes place at room temperature within 15 min., and at 50° C. within 5 min.

Anchor Block for N$^\alpha$Fmoc/tBu-solid-phase peptide synthesis

SYNTHESIS PATH A/EXAMPLE 1
N$^\epsilon$-Boc-Lys-Phe-Phe-α-rac-tert-butoxy-glycyl-βAla-OH
SEQ ID NO: 1 (LA.1.1) (MV)$^{(MV)}$
Structure

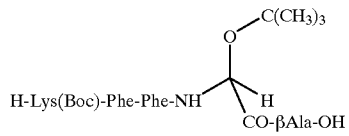

R$_1$: H-Lys(Boc)-Phe-Phe—
R2: CO-βAla-OH
R3: H
X: O
Y: tert-Butyl

SYNTHESIS PATH
N$^\alpha$-9-Fmoc-α-rac-hydroxy-glycin (LA.1.2)
Empirical Formula (C$_{17}$H$_{15}$NO$_5$)
10.74 g (45 10$^{-3}$ mol) aminoformic acid-9-fluorenylmethylester [Carpino, L. A.; Mansuor, E. M. E.; Cheng, C. H.; Williams, J. R., MacDonald, R.; Knapczyk, J. and Carman, E., *J. Org. Chem.*, 48 (1983) 661] are stirred together with 4.53 (50.10$^{-3}$ mol) glyoxalic acid hydrate in a mixture of 50 ml DCM and 40 ml TMF 2 d at RT. The solution is concentrated and the residue dissolved in ethyl acetate. It is extracted twice, each time with 150 ml water, and the organic phase is dried over MsSO$_4$. The organic phase is concentrated on the rotary evaporator and (LA.1.2) crystallised out of ethyl acetate/toluol.-Yield 12.55 g (89% of Th.).— $^1$H-NMR (400 MHz, CDCl$_3$): δ=7.81 (d, 2H, fluorenyl-H$^1$, $^3$J$_{H,H}$=7.30 Hz), 7.67 (d, 2H, fluorenyl-H$^4$, $^3$J$_{H,H}$=7.26 Hz), 7.4 (t, 2H, fluorenyl-H$^2$, $^3$J$_{H,H}$=7.30 Hz), 7.25 (t, 2H,fluoenyl-H$^3$, $^3$J$_{H,H}$=7.30), 5.95 (d, 1 H, NH), 5.47 (d,1H, NH—CHOH), 4.4(d,2H,CH—CH$_2$), $^3$J$_{H,H}$=6.67 Hz), 4.23 (t, 1 H, CH—CH$_2$, $^3$J$_{H,H}$=6.67 Hz).— $^{13}$C-NMR (75 MHz, CDCl$_3$): δ=168.9 (s, COOH), 154.7 (s, NH—COO), 143.7 (s, fluorenyl-C$_6$), 141.4 (s, fluorenyl-C$_5$), 128.2 (d, fluorenyl-C$_1$), 127.3 (d, fluorenyl-C$_4$), 124.7 (d, fluorenyl-C$_3$), 120.3 (d, fluorenyl-H$_2$), 78.9 (d, NH—CHOH), 68.1 (t, CH—CH$_2$), 46.8 (d, CH—CH$_2$).— MS (FAB, 3-NBA): m/z=315 (23, [M+H]$^\oplus$).
N$^\alpha$-9-Fmoc-α-rac-hydroxy-glycinbenzylester (LA.1.3)
Empirical Formula (C$_{24}$H$_{21}$NO$_5$)
1.57 g (5 10$^{-3}$ mol) (LA.1.2) and 815 mg (2.5 10$^{-3}$ mol) caesium carbonate are suspended in 17.6 ml 80% aqueous ethanol. The solution is concentrated to total and repeatedly (ex) resuspended in 30 ml absolute ethanol and concentrated. The residue is briefly dried in HV and suspended in 15 ml DMF. 627 μl (5 10$^{-3}$ mol benzyl bromide is added and shaken 2 d at RT. The reaction mixture is poured into iced water, and the aqueous phase extracted with ethyl acetate.

The organic phase is washed with saturated NaHCO$_3$—, saturated NaCl, 0.1 M hydrochloric acid and saturated NaCl solution and dried over MgSO$_4$. The organic phase is concentrated und (LA.1.3) crystallised out of dichloromethane/petroleum benzine—Yield: 1.85 g (92% of Th.).— $^1$H-NMR (400 MHz, CDCl$_3$): δ=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.4–7.2 (m, 9H, fluorenyl-H$^{2,3}$/phenyl-H), 5.95 (d, 1 H, NH), 5.47 (d, 1H, NH—C$\underline{H}$OH), 5.23 ('d', 2H COOC$\underline{H}_2$), 4.4 (d, 2H, CH—C$\underline{H}_2$), $^3J_{H,H}$=6.67 Hz), 4.23 (t, 1 H, C$\underline{H}$—CH$_2$) $^3J_{H,H}$=6.67 Hz).— $^{13}$C-NMR (75 MHz, CDCl$_3$): δ=168.5 (s, COOH), 154.2 (s, NH—COO), 143.7 (s, fluorenylC$_6$), 141.4 (s, fluorenyl-C$_5$), 135.2 (s, phenyl-H), 128.57/128.4/128.1/127.1/125.1/120.0(d,fluorenyl-C/phenyl-C), 78.4 (d, NH—C$\underline{H}$OH), 67.2 (t, COOC$\underline{H}_2$), 67.1 (t CH—C$\underline{H}_2$), 47.1 (d, C$\underline{H}$—CH$_2$).

N$^\alpha$-9-Fmoc-α-rac-tert-butoxy-glycinbenzylester (LA.1.4)
Empirical Formula (C$_{28}$H$_{29}$NO$_5$)

Method 1: 100 mg (25 10-5 mol) (LA.1.3) are dissolved in 500 μl absolute dioxane und 250 μl absolute diethyl ether in a thick-walled glass flask and 5 Ml conc. sulphuric acid added. About 250 μl isobutene is condensed in at 45° and the flask is closed. It is shaken for 8 h at 4° C. and the reaction mixture poured into 50 ml ges. NaHCO$_3$ solution. It is extracted 2× with 100 ml ethyl acetate, and the oeganis phase 2× washed respectively with 100 ml saturated NaCl—, 10% citric acid-, saturated NaCl solution and dried over MgSO+4. (LA.1.4) is isolated by RP-C$_{18}$-HPLC with water/acetonitrile.— Yield: (30–50% of Th.)

Method 2: 100 mg (25 10$^{-5}$ mol) (LA.1.3) are converted under reflux in 2 ml absolute THF with 55 μl dist. (75 10$^{-5}$ mol) thionyl chloride over 1 h. The reaction mixture is fully concentrated and briefly treated in HV. 2 mi abs. tert-butanol und 42 μl (25 10$^{-5}$ mol) ethyl diisopropylamine are added and refluxed 2 h. The reaction mixture is poured into a saturated aqueous NaCl solution and the aqueous phase 2× extracted with 100 ml ethyl acetate. The organic phase is dried over MgSO$_4$ and concentrated. (LA.1.4) is cleaned up either wird RP-C18-HPLC chromatographically to homogeneity or used as a raw product (>95% content (LA.1.4) in the further reaction.— $^1$H-NMR (400 MHz, CDCl$_3$): δ=7.81 (d, 2H, fluorenyl-H$^1$,$^3J_{H,H}$=7.30 Hz), 7.67(d,2H, fluorenylH$^4$,$^3J_H$. 7.26 Hz), 7.4–7.2 (m, 9H, fluorenyl-H$^{2,3}$/phenyl-H), 5.95 (d, 1H, NH), 5.47 (d, 1H, NH—C$\underline{H}$OH), 5.23 ('d', 2H COOC$\underline{H}_2$), 4.4 ('m' (dt), 2H, CH—C$\underline{H}_2$ ), $^3J_{H,H}$=6.67 Hz), 4.23(t, 1H, C$\underline{H}$—CH2, $^3J_{H,H}$=6.67 Hz), 1.25 (s, 9H, C(CH$_3$)$_3$).— $^{13}$C-NMR (75 MHz, CDCl$_3$): δ=168.5 (s, COOH), 154.2 (s, NH—COO), 143.7 (s, fluorenylC$_6$), 141.4 (s, fluorenyl-C$_5$), 135.2 (s, phenyl-H), 128.57/128.4/128.1/127.1/125.1/120.0 (d, fluorenyl-C/phenyl-C), 78.4 (d, NH—C$\underline{H}$OH), 74.6 (s, $\underline{C}$(CH$_3$)$_3$), 67.2 (t, COO—C$\underline{H}_2$), 67.1 (t CH—C$\underline{H}$2), 47.1 (d, C$\underline{H}$—CH$_2$), 28.2 (q, C(CH$_3$)$_3$).— MS (FAB, 3-NBA): m/z=461 (27, [M+H]$^\oplus$).

N$^\alpha$-9-Fmoc-α-rac-tert-butoxy-glycin (LA.1.5)$^{(AB)}$
Empirical Formula (C$_{21}$H$_{23}$NO$_5$)

115 mg (25 10$^{-5}$ mol) (LA.1.4) are dissolved in 3 ml abs. ethanol/ethyl acetate (1:2). A spatula tip of palladium/activated carbon (Fluka) is added and hydrogen is passed through the solution for 25 min. The catalyst is filtered off and (LA.1.5) RP-Cl8-HPLC chromatograpically isolated. Yield: 60.45 mg(70% fo Th.).— $^1$H-NMR (400 MHz, CDCl$_3$) δ=7.81 d, 2H, fluorenyl-H$^1$, $^3J_{H,H}$=7.30 Hz), 7.67 (d, 2H, fluorenyl-H$^4$, $^3J_{H,H}$=7.26 Hz), 7.42 (t, 2H, fluorenyl-H$^2$, $^3J_{H,H}$=7.30 Hz), 7.25 (t (fine division d), 2H, fluorenyl-H$^3$, $^3J_{H,H}$=7.30), 5.87 (d, 1H, NH), 5.47 (d, 1H, NH—C$\underline{H}$OH), 4.4 ('m', 2H, CH—C$\underline{H}_2$) $^3J_{H,H}$=6.67 Hz), 4.23 (t, 1H, C$\underline{H}$—CH2) $^3J_{H,H}$=6.67 Hz), 1.25 (s, 9H, c(CH$_3$)$_3$).— $^{13}$C-NMR (75 MHz, CDC$_3$): δ=168.5 (s, COOH), 154.2 (s, NH—COO), 143.7 (s, fluorenyl-C$_6$), 141.4 (s, fluorenyl-C$_5$), 128.2 (d, fluorenyl-C$_1$), 127.3 (d, fluorenyl-C$_4$), 124.7 (d, fluorenyl-C$_3$), 120.3 (d, fluorenyl-H$_2$),78.4 (d, NH—$\underline{C}$HOH), 74.6 (s, $\underline{C}$(CH$_3$)$_3$), 67.1 (t CH—C$\underline{H}_2$), 47.1 (d, C$\underline{H}$—CH$_2$),28.2 (q, C(CH$_3$)$_3$).— MS (FAB, 3-NBA): m/z= 370 (37, [M+H]$^\oplus$).

N$^\epsilon$-Boc-Lys-Phe-Phe-α-rac-tert-butoxy-glycyl-βAla-OH SEQ ID NO: 1 (LA.1.1)$^{(Mv)}$
Empirical Formula (C$_{38}$H$_{56}$N$_6$O$_9$)

The protected peptide (LA.1.1) is built up according to conventional peptide synthesis conditions on an o-chlorotrityl-functionalized resin using (LA.1.5) and separated from the carrier as normal. The amino function of the protected N.O-acetal is here released with 10% morpholin/5% triethylammonium chloride/DMF.— MS (FAB, thioglycerin): m/z=740 (5, [M+H]$^\oplus$).

Application
The protected peptide (LA.1.1)displays total stability to 20% piperidine/DMF (indicated by quantitative UV/VIS-analysis of the individual coupling steps, and by treatment of the protected peptide (LA.1.1) in solution with the above-named reagent). After division of the hydroxyl protective group according to normal procedures (and simultaneously of the Boc protective group of the lysyl residue) the peptide thus deprotected is treated with buffer systems (a), (b) and (g). The deprotected model compound decomposes in the desired way into the peptidamide H-Lys-Phe-Phe-NH$_2$.

SYNTHESIS PATH A/EXAMPLE 2
H-Lys(Boc)-Phe-Phe-α-rac-(MOM)oxy-β-trifluoralanine-βAla-OH SEQ ID NO: 2 (LA.2.1)
Structure

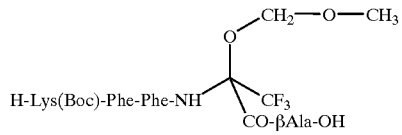

SYNTHESIS PATH
N$^\alpha$-9-Fmoc-α-hydroxy-β.β.β-trifluoralanine methylester (LA.2.2)
Empirical Formula (C$_{19}$H$_{16}$F$_3$NO$_5$)

Similarly (LA.1.2) reaction was brought about with aminoformic acid-9-fluorenylmethylester in ethyl acetate over 4 d with 3.3.3-trifluoropyruvic acid methylester. The mixture is poured into a mixture of diethylether/petroleum benzine and allowed to stand at −20° C. The crystallisate is filtered off and the residue concentrated.— Yield: (75% of theoretical).— $^1$H-NMR (400 MHz, CDCl$_3$): δ=7.81 (d, 2H, fluorenyl-H$^1$,$^3J_{H,H}$=7.30 Hz), 7.67 (d, 2H, fluorenyl-H$^4$, $^3J_{H,H}$=7.26 Hz), 7.4 (t, 2H, fluorenyl-H$^2$ $^3J_{H,H}$=7.30 Hz), 7.25 (t, 2H, fluorenyl-H$^3$, $^3J_{H,H}$=7.30), 5.95 (s, 1 H, NH), 4.4 (d, 2H, CH—C$\underline{H}_2$), $^3J_{H,H}$=6.67 Hz), 4.23 (t, 1H, C$\underline{H}$—CH$_2$, $^3J_{H,H=}$6.67 Hz), 3.86 (s, 3H, CH$_3$).— $^{13}$C-NMR (75 MHz, CDCl$_3$): δ=164.3 (s, $\underline{C}$OOCH3), 154.0 (s, NH $\underline{C}$OO), 143.7 (s, fluorenyl-C$_6$), 141.4 (s, fluorenyl-C$_5$), 128.2 (d, fluorenyl-C$_1$) 127.3 (d, fluorenyl-C$_4$), 124.7 (d, fluorenyl-C$_3$), 120.3 (d, fluorenyl-H$_2$), 93.1 (d, NH—$\underline{C}$(CF$_3$)OH), 67.8 (t, CH—C$\underline{H}_2$), 54.0 (q, COO$\underline{C}$H$_3$), 47.0 (d, C$\underline{H}$—CH$_2$).— $^{19}$F-NMR (376 MHz, CDCl$^3$): δ=−79.4 (s, CF$_3$).— MS (FAB, 3-NBA): m/z=395 (23, [M+H]$^\oplus$).

Nα-9-Fmoc-α-(methoxymethyl)oxy-β.β.β-trifluoralanine methylester (LA.2.3)

Empirical Formula (C₂₁H₂₃NO₄S)

(PA.2.2) is presented in a mixture of der 10 times the quantity of formaldehyde dimethylacetal and the same quantity of absolute chloroform in the presence of a large excess of phosphorus pentoxide. The reaction mixture is poured into a saturated sodium chloride solution and extracted 2× with ethyl acetate. The organic phase is dried over $Na_2SO_4$ and concentrated. The residue is dissolved in ethanol and water is rapidly added. The milky solution is carefully concentrated by half and left at 4° C. over 4 h. The white solid matter is filtered off and dried in HV.— Yield: (74% of theoretical).— ¹H-NMR (400 MHz, CDCl₃): δ=7.81 (d, 2H, fluorenyl-H¹,³$J_{H.H}$=7.30 Hz), 7.67 (d, 2H, fluorenyl-H⁴, ³$J_{H.H}$=7.26 Hz), 7.4 (t, 2H, fluorenyl-H² ³$J_{H.H}$=7.30 Hz), 7.25 (t, 2H,fluorenyl-H³, ³$J_{H.H}$=7.30), 5.95 (s, 1 H, NH), 5.05 (d, 1 H, O—CH₂—O, ²$J_{H.H}$=7.30 Hz), 4.82 (d,1H, O—CH₂—O, ²$J_{H.H}$=7.30 Hz), 4.4 ('ddd', 2H, CH—C$\underline{H}$₂, ³$J_{H.H}$=6.70 Hz), 4.20 (t, 1H, C$\underline{H}$—CH₂), ³$J_{H.H}$=6.70 Hz), 3.86 (s, 3H, CH₃), 3.40 (s, 3H, CH₃O).— ¹³C-NMR (75 MHz, CDCl₃): δ=164.3 (s, COOCH₃), 154.0 (s, NH—COO), 143.7 (s, fluorenyl-C₆), 141.4 (s, fluorenyl-C₅), 128.2 (d,fluorenyl-C₁), 127.3 (d, fluorenyl-C₄), 124.7 (d, fluorenyl-C₃), 120.3 (d,fluorenyl-H₂), 94.2 (d, NH—$\underline{C}$(CF₃)OH), 77.5 (t, O—CH₂O), 67.8 (t, CH—C$\underline{H}$₂), 56.6 (q, CH₃O), 54.0 (q, COOC$\underline{H}$₃), 47.0 (d, C$\underline{H}$—CH2).— ¹⁹F-NMR (376 MHz,CDCl₃): δ=−80.1 (s, CF₃).— MS (FAB,3-NBA): m/z=395 (23, [M+H]⊕).

Nα-9-Fmoc-α-(methoxymethyl)oxy-β.β.β-trifluoralanine (LA.2.4)$^{(AB)}$

Empirical Formula (C₂₀H₁₈F₃NO₆)

The carboxylic function of (LA.2.3) was released in acetone/water with catalysis of LiOH. The product was chromatographically isolated RP-C₁₈-HPLC.— Yield: (65% of theoretical).— ¹H-NMR (400 MHz, CDCl₃): δ=7.81 (d, 2H,fluorenyl-H¹,³$J_{H.H}$=7.30 Hz), 7.67 (d, 2H, fluorenyl-H⁴, ³$J_{H.H}$=7.26 Hz), 7.4t, 2H, fluorenyl-H², ³$J_{H.H}$=7.30 Hz), 7.25 (t, 2H, fluorenyl-H₃, ³$J_{H.H}$=7.30),5.95(s, 1 H, NH), 5.05 (d,1 H, O—CH₂—O,²$J_{H.H}$=7.30 Hz), 4.82 (d, 1 H, O—CH₂—O, ²$J_{H.H}$=7.30 Hz), 4.4 ('ddd', 2H, CH—C$\underline{H}$₂) ³$J_{H.H}$=6.70 Hz), 4.20 (t, 1 H, C$\underline{H}$—CH₂) ³$J_{H.H}$=6.70 Hz), 3.40 (s, 3H, CH₃O).— ¹³C-NMR (75 MHz, CDCl₃): δ=164.3 (s, COOH), 154.1 (s, NH—COO), 143.7 (s, fluorenyl-C₆), 141.4 (s, fluorenyl-C₅), 128.2 (d, fluorenyl-C₁), 127.3 (d, fluorenyl-C₄), 124.7 (d, fluorenyl-C₃), 120.3 (d, fluorenyl-H₂), 94.2 (d, NH—$\underline{C}$(CF₃)OH), 77.0 (t, O—CH₂—O), 67.8 (t, CH—C$\underline{H}$₂), 56.6 (q, CH₃O), 54.0 (q, COOC$\underline{H}$3), 47.0 (d, C$\underline{H}$—CH₂).— ¹⁹F-NMR (376 MHz, CDCl₃): δ=−79.4 (s, CF₃)—MS (FAB, 3-NBA): m/z=426 (23, [M+H]⊕).

H-Lys(Boc)-Phe-Phe-α-rac-methoxy-β.-trifluoralanine-βalanin SEQ ID NO: 3 (LA.2.1)$^{(MV)}$ Empirical Formula (C₃₇H₄₂F₃N₆O₁₀)

According to general peptide synthesis methods, (LA.2.1) is built up on an o-chlorotrityl-functionalised resin and und separated as a protected peptide according to known methods.— MS (FAB): M/Z (3-NBA)=789 ([M+H]⊕).

Application

Treatment with 95% TFA/2.5% TIBS/2.5% water leads to simultaneous deprotection of the BOC protective group of the lysyl residue and of the hydroxyl function of the N.O-acetal. This deprotected peptide decomposes in the desired way into the peptidamide by treatment with buffer system (a) to (g). Reaction takes place within 15 min. At 50° C.

SYNTHESIS PATH A/EXAMPLE 3

H-Lys(Boc)-Phe-Phe-α-rac-(alkoxymethyl)oxyglycyl-βAla SEQ ID NO: 4 (LA.3.1)$^{(MV)}$ Structure

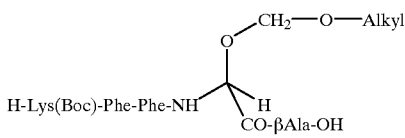

R₁: H-Lys(Boc)-Phe-Phe—
R₂: CO-βAla-OH
R₃: H
X: O
Y: Alkoxymethyl

Different protective groups, based on an acetalic structure, were introduced into the underlying anchor block. The stability of the protected N.O-acetal with free amino function is so low that the protected N.O-Acetal to a large extent decomposes during the basic division of the Fmoc protective group before it can be brought to react with the following amino acid residue. Only traces of the desired model compound (LA.3.1) can be isolated. The tests are carried out both in solution with the corresponding benzyl esters and also on the solid carrier with the aid of the anchor blocks. These compounds and the corresponding anchor blocks are recorded for the sake of completeness.

SYNTHESIS PATH

Nα-9-Fmoc-α-(methoxymethyl)oxy-glycinebenzylester (LA.3.2)

Empirical Formula (C₂₁H₂₃NO₄S)

Similarly to (LA.2.3), (LA.3.2) is synthesised from (LA.1.3).— Yield: 1.85 g (92% of theoretical).— ¹H-NMR (400 MHz, CDCl₃): δ=7.81 (d, 2H, fluorenyl-H¹),³$J_{H.H}$= 7.30 Hz), 7.67 (d, 2H, fluorenyl-H⁴, ³$J_{H.H}$=7.26 Hz), 7.4–7.2 (m, 9H, fluorenyl-H²·³/phenyl-H), 5.95 (d, 1 H, NH, ³$J_{H.H}$= 7.31 Hz), 5.47 (d, 1H, NH—C$\underline{H}$OH, ³$J_{H.H}$=7.31 Hz), 5.23 (s, 2H COOC$\underline{H}$₂), 4.95 (d, 1H, O—CH₂—O, ²$J_{H.H}$=7.26 Hz), 4.82 (d, 1H, O—CH₂—O, ²$J_{H.H}$=7.24 Hz), 4.4 ('m' (dt), 2H, CH—C$\underline{H}$2), ³$J_{H.H}$=6.67 Hz), 4.23 (t, 1H, C$\underline{H}$—CH₂, ³$J_{H.H}$= 6.67 Hz), 3.40 (s, 3H, CH₃O).— ¹³C-NMR (75 MHz, CDCl₃): δ=168.5 (s, COOH), 154.2 (s, NH—COO), 143.7 (s, fluorenyl-C₆), 141.4 (s, fluorenyl-C₅), 135.2 (s, phenyl-H),128.57/128.4/128.1/127.1/125.1/120.0(d, fluorenyl-C/phenyl-C), 78.4 (d, NH—$\underline{C}$HOR), 77.0 (t, O—CH₂—O), 67.2 (t, COO—C$\underline{H}$₂), 67.1 (t CH—C$\underline{H}$₂), 57.2 (q, CH₃O), 47.1 (d, C$\underline{H}$—CH₂).— MS (FAB,3-NBA): m/z 405 (28, [M+H]⊕).

N(α-9-Fmoc-α-(methoxymethyl)oxy-glycin (LA.3.3)$^{(AB)}$

Empirical Formula (C₂₁H₂₃NO₄S)

Similarly to (LA.1.5), (LA.3.3) is synthesised from (LA.3.2). Yield: 1.85 g (92% of theor.).— ¹H-NMR (400 MHz, CDCl₃): δ=7.81 d, 2H, fluorenyl-H¹, ³$J_{H.H}$=7.30 Hz), 7.67 (d, 2H, fluorenyl-H⁴, ³$J_{H.H}$=7.26 Hz), 7.42 (t, 2H) fluorenyl-H², ³$J_{H.H}$=7.30 Hz), 7.25 (t (fine division d), 2H, fluorenyl-H³,³$J_{H.H}$=7.30), 5.87 (d, 1H, NH), 5.47 (d, 1 H, NH—C$\underline{H}$OH), 4.94 (d, 1 H, O—CH₂—O, ²$J_{H.H}$=7.20 Hz), 4.75 (d, 1H, O—CH₂—0, ²$J_{H.H}$=7.20 Hz), 4.4 ('m', 2H, CH—C$\underline{H}$₂ ³$J_{H.H}$=6.67 Hz), 4.23 (t, 1H, C$\underline{H}$—CH₂, ³$J_{H.H}$= 6.67 Hz), 3.40 (s, 3H, CH₃O).— ¹³C-NMR (100 MHz, CDCl₃): δ=168.5 (s, COOH), 154.2 (s, NH—COO), 143.7 (s, fluorenyl-C₆), 141.4 (s, fluorenyl-C₅), 128.2 (d, fluorenyl C₁), 127.3 (d, fluorenyl-C₄), 124.7 (d, fluorenyl-C₃), 120.3 (d, fluorenyl-H₂), 78.4 (d, NH—$\underline{C}$HOH), 77.0 (t, O—CH₂—O), 67.1 (t CH—C$\underline{H}$₂), 54.1 (q, CH₃O), 47.1 (d, C$\underline{H}$—CH₂).— MS (FAB, 3-NBA): m/z=370 (37, [M+H]⊕).

Nα-9-Fmoc-α-(methoxyethoxymethyl)oxy-glycinebenzylester (LA.3.4)

Empirical Formula ($C_{21}H_{23}NO_4S$)

(LA.3.4)is synthesized from (LA.1.3) by conversion with methoxyethoxymethylchloride (Fluka) with catalysis by 1.0 eq. Ethyl diisopropylamine in DCM. Yield: 1.85 g (92% of theor.).— $^1$H-NMR (400 MHz, $CDCl_3$):δ=7.81 (d, 2H fluorenyl-H$^4$,$^3J_{H,H}$=7.30 Hz), 7.67 (d, 2H, fluorenyl-H$^4$, $^3J_{H,H}$=7.26 Hz), 7.4–7.2 (m, 9H, fluorenyl-H$^{2,3}$/phenyl-H), 5.87 (d, 1H, NH), 5.47 (d, 1H, NH C$\underline{H}$OH), 5.23 ('d', 2H, COOC$\underline{H}_2$), 4.94 (d, 1 H, O—CH$_2$—O, $^2J_{H,H}$=7.20 Hz), 4.75 (d, 1 H, O—CH$_2$—O, $^2J_{H,H}$=7.20 Hz), 4.4 ('m', 2H, CH—C $\underline{H}$hd 2, $^3J_{H,H}$=6.67 Hz),4.23 (t, 1 H, C$\underline{H}$—CH$_2$), $^3J_{H,H}$=6.67 Hz), 3.85 (AB-t, 4H, C$\underline{H}_2$—C$\underline{H}_2$), 3.40 (s, 3H,CH$_3$O).— $^{13}$C-NMR (100 MHz, CDCl$_3$): δ=166.7 (s, COOH), 155.4 (s, NH—COO), 143.6 (s, fluorenyl-$C_6$), 141.4 (s, fluorenyl-$C_5$), 134.7 (s, phenyl-H), 128.5–120.0 (5 signals) (d, fluorenyl-H/phenyl-H), 78.9 (d, NH—$\underline{C}$HOH), 77.0 (t, O—CH$_2$—O), 67.9 (t, CH—C$\underline{H}_2$), 67.5 (t, COO—C$\underline{H}$2), 67.4 (t, $\underline{C}$H2—C$\underline{H}_2$), 46.9 (d, C$\underline{H}$—CH$_2$), 30.9 (q, CH$_3$O).— MS (FAB, 3-NBA): m/z=370 (37, [M+H]$^\oplus$).

N$^\alpha$-9-Fmoc-α-(trimethylsilylethoxymethyl)oxy-glycinebenzylester (LA.3.5)

Empirical Formula ($C_{21}H_{23}NO_4S$)

(LA.3.4)is synthesized from (LA.1,3) by conversion with trimethylsilylethoxymethylchloride (Fluka) with catalysis by 1.0 eq. ethyldiisopropylamine in DCM/DMF=6/1.— Yield: 1.85 g (92% of theoretical).— $^1$H-NMR (400 MHz, CDCl$_3$): δ=7.81 (d, 2H, fluorenyl-H$^1$, $^3J_{H,H}$=7.30 Hz), 7.67 (d, 2H,fluorenyl-H$^4$, $^3J_{H,H}$=7.26 Hz),7.4–7.2 (m, 9H, fluorenyl-H$^{2,3}$/phenyl-H), 5.87 (d,1H,NH), 5.47 (d,1H, NH—C$\underline{H}$OH), 5.24 ('d',2H,COOC$\underline{H}_2$), 4.94 (d,1H,O—CH$_2$—O, $^2J_{H,H}$=7.20 Hz), 4.75 (d,1H,O—CH$_2$—O, $^2J_{H,H}$= 7.20 Hz), 4.4('m', 2H, CH—C$\underline{H}_2$, $^3J_{H,H}$=6.67 Hz), 3.82 (AB-t, 4H, C$\underline{H}_2$—C$\underline{H}_2$), 4.23 (t, 1 H, C$\underline{H}$—CH$_2$$^3J_{H,H}$=6.67 Hz), 0.1 (s, 3H, Si(CH$_3$)$_3$).— $^{13}$C-NMR (100 MHz, CDCl$_3$): δ=166.7 (s, COOH), 155.4 (s, NH—COO), 143.6 (s, fluorenyl-$C_6$), 141.4 (s, flourenyl-$C_5$), 134.7 (s, phenyl-H), 128.5–120.0 (5 signals) (d, fluorenyl-H/phenyl-H), 78.9 (d, NH—$\underline{C}$HOH), 77.0 (t, COO—CH$_2$—$\underline{O}$), 67.9 (t, CH—C $\underline{H}_2$), 67.4 (t, $\underline{C}$H$_2$—C$\underline{H}_2$), 67.2 (t, COO—C$\underline{H}_2$), 46.9 (d, C $\underline{H}$—CH$_2$), 2.0 (q, Si(CH$_3$)$_3$).— MS (FAB, 3-NBA): m/z= 370 (37, [M+H]$^\oplus$).

N$^\alpha$-9-Fmoc-α-(trimethylsilylethoxymethyl)oxy-glycine (LA.3.6) (AB)

Empirical Formula ($C_{21}H_{23}NO_4S$)

Similarly to (LA.2.3), (LA.3.2) is synthesised from (LA.1.3).— Yield: 1.85 g (96% of th.).— $^1$H-NMR (400 MHz, CDCl$_3$): δ=7.81 d, 2H, fluorenyl-H$^1$, $^3J_{H,H}$=7.30 Hz), 7.67 (d, 2H, fluorenyl-H$^4$, $^3J_{H,H}$=7.26 Hz), 7.42 (t, 2H, fluorenyl-H$^2$, $^3J_{H,H}$=7.30 Hz), 7.25 (t (fine division d), 2H, fluorenyl-H$^3$, $^3J_{H,H}$=7.30), 5.87 (d, 1H, NH), 5.47 (d, 1H, NH—C$\underline{H}$OH), 4.94 (d, 1H, O—CH$_2$—O, $^2J_{H,H}$=7.20 Hz), 4.75 (d, 1 H, O—CH$_2$—O, $^2J_{H,H}$=7.20 Hz), 4.4 ('m', 2H, CH—CH$_2$, $^3J_{H,H}$=6.67 Hz), 3.82 (AB-t, 4H, C$\underline{H}$2—C$\underline{H}$2), 4.23 (t, 1H, C$\underline{H}$—CH$_2$, $^3J_{H,H}$=6.67 Hz), 0.1 (s, 3H, Si(CH$_3$ )$_3$).— $^{13}$C-NMR (100 MHz, CDCl$_3$): δ=168.5 (s, COOH), 154.2 (s, NH—COO), 143.7 (s, fluorenyl-$C_6$), 141.4 (s, fluorenyl-$C_5$), 128.2 (d, fluorenyl-$C_1$), 127.3 (d, fluorenyl-$C_4$), 124.7 (d, fluorenyl-$C_3$), 120.3 (d, fluorenyl-H$_2$), 78.9 (d, NH—$\underline{C}$HOH), 77.0 (t, O—CH$_2$—O), 67.9 (t, CH—C$\underline{H}$2), 67.4 (t,$\underline{C}$H$_2$—C$\underline{H}_2$), 46.9 (d, C$\underline{H}$—CH$_2$), 2.0 (q, Si(CH$_3$)$_3$).

SYNTHESIS PATH A/EXAMPLE 4

H-Lys(Boc)-Phe-Phe-α-rac-tert-butyl-dimethylsilyloxyglycyl-βAla SEQ ID NO: 5 (LA.4.1)

Structure

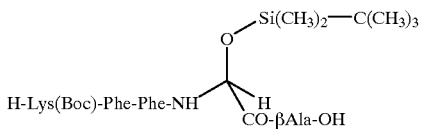

R$_1$: H-Lys(Boc)-Phe-Phe—
R$_2$: CO-βAla-OH
R$_{3+}$: H
X: O
Y: tert-butyldimethylsilyl N$^\alpha$-9-Fmoc-α-tert-butyl-dimethylsilyloxy-glycinebenzylester (LA.4.2)

Empirical Formula ($C_{30}H_{35}NO_5Si$)

100 mg (25 10-5 mol) (LA.1.3) and 52.5 mg (37.5 10-5 mol) tert-butyldimethyisilyl chloride are dissolved in a mixture of 2 ml absolute DMF und 2 ml dichloromethane, while heating. 42.2 μl ethyldiisopropylamine are added and refluxed for 12 h. The product is chromatographically isolated according to usual procedures RP-Ci,-HPLC.— Yield: 84 mg (63–67% of theor.).— $^1$H-NMR (400 MHz, CDCl$_3$): δ=7.81 (d, 2H, fluorenyl-H$^1$, $^3J_{H,H}$=7.30 Hz), 7.67 (d, 2H, fluorenyl-H$^4$ $^3J_{H,H}$=7.26 Hz), 7.4–7.2 (m, 9H, fluorenyl-H$^{2,3}$/phenyl-H), 5.95 (d, 1H, NH), 5.47 (d, 1 H, NH—C$\underline{H}$OH), 5.23 ('d', 2H COOC$\underline{H}_2$), 4.4 ('m' (dt), 2H, CH—C$\underline{H}_2$), $^3J_{H,H}$=6.67 Hz), 4.23 (t, 1H, CH—C$\underline{H}$2, $^3J_{H,H}$=6.67 Hz), 0.85 (s, 9H, SiC(CH$_3$)$_3$), 0.15 ('d, 6H, Si(CH$_3$)$_2$).— $^{13}$C-NMR (75 MHz, CDCl$_3$): δ=168.5 (s, COOH), 154.2 (s, NH—COO), 143.7 (s, fluorenyl-$C_6$), 141.4 (s, fluorenyl-$C_5$), 135.2 (s, phenyl-H), 128.57/128.4/128.1/127.1/125.1/120.0 (d, fluorenyl-C/phenyl-C), 78.4 (d, NH—$\underline{C}$HOH), 70.1 (S, Si$\underline{C}$(CH$_3$)$_3$), 67.2 (t, COO—C$\underline{H}_2$), 67.1 (t CH—C$\underline{H}_2$), 47.1 (d, C$\underline{H}$—CH$_2$), 25.2 (q, C(CH$_3$)$_3$), 4.0 (q, Si(CH$_3$)$_2$).— MS (FAB, 3-NBA): m/z=461 (27, [M+H]$^\oplus$).

N$^\alpha$9-Fmoc-α-tert-butyl-dimethyisilyloxy-glycine (LA.4.3) (AB)

Empirical Formula ($C_{23}H_{29}NO_5Si$)

Similarly to (LA.1.5), (LA.4.2) is treated in the presence of Pd/activated carbon in ethyl acetate/EtOH in a hydrogen flow. Yield: 570 mg (92% of theor.; dichloromethane/petroleum benzine).— $^1$H-NMR (400 Mhz, CDCl$_3$): δ=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.4–7.2 (m, 9H, fluorenyl-H$^{2,3}$/phenyl-H), 5.95 (d, 1H, NH), 5.47 (d, 1H, NH—C$\underline{H}$OH), 5.23 ('d', 2H COOC$\underline{H}_2$), 4.4 ('m' (dt), 2H, CH—C$\underline{H}_2$), $^3J_{H,H}$=6.67 Hz), 4.23 (t, 1H, C$\underline{H}$—CH$_2$, $^3J_{H,H}$=6.67 Hz), 0.85 (s, 9H, SiC(CH$_3$)$_3$), 0.15 ('d', 6H, Si(CH$_3$)$_2$).— $^{13}$C-NMR (75 MHz, CDCl$_3$): δ=168.5 (s, COOH), 154.2 (s, NH—COO), 143.7 (s, fluorenyl-$C_6$), 141.4 (s,fluorenyl-$C_5$),135.2(s, phenyl-H), 128.57/128.4/128.1/127.1/125.1/120.0(d, fluorenyl-C/phenyl-C), 78.4 (d, N H—CHOH), 69.9 (s, Si $\underline{C}$(CH$_3$)$_3$), 67.2 (t, COO—C$\underline{H}_2$), 67.1 (t CH—C$\underline{H}_2$), 47.1 (d, C$\underline{H}$—CH$_2$), 28.2 (q, C(CH$_3$)$_3$), 4.0 (q, Si($\underline{C}$H$_3$)$_2$).— MS (FAB, 3-NBA): m/z=461 (27, [M+H]$^\oplus$).

H-Lys(Boc)-Phe-Phe-α-rac-(TBDMS)oxyglycyl-βAla-OH SEQ ID NO:6 (LA.4.1)$^{(MV)}$

Empirical Formula ($C_{40}H_{52}N_6O_9Si$)

The protected peptide (LA.4.1) is built up according to normal peptide synthesis conditions on an o-chlorotrityl-functionalized resin, using (LA.4.3), and divided from the carrier as usual. The amino function of the protected N.O-acetals is here released with 10% morpholine/5% triethylammonium chloride/DMF.— MS (FAB, 3-NBA): m/z=788 (27, [M+H]$^\oplus$).

Application

The protected peptide (LA.4.1) displays total stability against 20% piperidine/DMF (shown by quantitative UV/VIS-analysis of the individual coupling steps, and by treatment of the protected peptide (LA.4.1)in solution with 20% piperidine/DMF). After division of the hydroxyl protective group according to usual procedures (and simultaneously the Boc protective group of the lysyl residue), the deprotected peptide is treated with buffer system (a), (b) and (g). The deprotected model compound decomposes in the desired way into the peptidamide H-Lys-Phe-Phe-$NH_2$.

SYNTHESIS PATH A/EXAMPLE 5
H-Lys(Boc)-Phe-Phe-α-rac-ethylthio-glycyl-βAla-OH SEQ ID NO: 7 (LA.5.1)
Structure

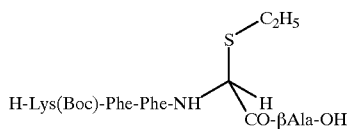

$R_1$: H-Lys(Boc)-Phe-Phe—
$R_2$: CO-βAla-OH
$R_3$: H
X: S
Y: Ethyl—

SYNTHESIS PATH
$N^\alpha$-9-Fmoc-α-ethylthio-glycin (LA.5.2)$^{(AB)}$
Empirical Formula ($C_{20}H_{21}NO_4S$)

522 mg (1.67 $10^{-3}$ mol) (LA.1.2) are suspended in 1.66 ml glacial acetic acid and und 619 μl (6.@ 7 $10^{-3}$ mol) ethylmercaptan and 166 μl conc. Sulphuric acid are successively added at 0° C. It is stirred for 1 h at 0° C. and 24 h at RT, the reaction mixture is poured into iced water and extracted 3× with 100 ml ethyl acetate. The organic phase is neutrally washed with saturated NaCl solution dried over $Na_2SO_4$ dried and concentrated. The oily residue is dissolved in a little DCM and crystallised by the addition of petroleum benzine as a solid white material, by lengthy standing at −20° C. Yield:570 mg (87% of theor.).— $^1$H-NMR (400 MHz, $CDCl_3$): δ=7.81 (d, 2H, fluorenyl-$H^1$, $^3J_{H,H}$=7.30 Hz), 7.67 (d, 2H, fluorenyl $H^1$, $^3J_{H,H}$=7.26 Hz), 7.4(t, 2H, fluorenyl-H×JH.H=7.30 Hz), 7.25 (t, 2H, fluorenyl-$H^3$, $^3J_{H,H}$=7.30), 5.95 (d, 1H, NH), 5.47 (d, 1H, NH—C$\underline{H}$OH), 4.40 (d, 2H, CH—C$\underline{H}_2$ $^3J_{H,H}$=6.67 Hz), 4.23 (t, 1 H, C$\underline{H}$—CH2) $^3J_{H,H}$=6.67 Hz), 2.55 (q, 2H, S—$CH_2$), 1.23 (t, 3H,$CH_3$).— $^{13}$C-NMR (75 MHz, $CDCl_3$): δ=168.9 (s, COOH), 154.7 (s, NH—COO), 143.7 (s, fluorenyl-$C_6$), 141. 4 (s, f luorenyl-$C_5$), 128.2 (d, fluorenyl-$C_1$), 127.3 (d, fluorenyl-$C_4$), 124.7 (d, fluorenyl-$C_3$), 120.3 (d, fluorenyl-$H_2$), 78.9 (d, NH—$\underline{C}$HOH), 68.1 (t, CH—C$\underline{H}$2), 46.8 (d, C$\underline{H}$—$CH_2$), 27.4 (t, S—$CH_2$), 15.2 (q, $CH_3$).— MS (FAB, 3-NBA): m/z=315 (23, [M+H]$^\oplus$).
H-Lys(Boc)-Phe-Phe-α-rac-ethylthio-glycyl-βAla-OH SEQ ID NO: 7 (LA.5.1)$^{(MV)}$
Empirical Formula ($C_{36}H_{42}N_6O_8S$)

The protected model peptide (LA.5.1) was synthesised on o-chlorotrityl-functionalised polystyrol in stages using the linker block (LA.5.2). The amino function on the linker block (LA.5.2) is deprotected with 20% piperidine/DMF. Cleaning is effected chromatograpically RP-$C_{18}$-HPLC. Both diastereomers are chromatographically separable.— MS (FAB) m/z (3-NBA)=718 ([M+H]$^\oplus$).

Appplication

During synthesis of the protected peptide (LA.5.1), the N.S=acetal deprotected on nitrogen and protected at the thiol function was passed through. This is stable against 20% piperidine/DMF and can be brought to reaction with the following amino acid derivate without appreciable disruption of the N.S-acetal structure. The peptide (LA.5.1) split from the resin was in addition treated with the splitting reagent fro 24 h. No alteration in the educt is observed. Treatment of (LA.5.1) with 95% TFA/2.5% TIBS/2.5% $H_2O$ leads to splitting of the Boc protective group in the lysin residue. Under these conditions the thiol function of the N.S-acetal remains protected. The partially deprotected peptide is treated with an excess of 2% aqueous Hg-II-chloride together with 10% aqueous acetic acid. These conditions lead to transfer of the N.S-acetal into an N.O-acetal. This is stable under acidic aqueous conditions. The N.O-acetal thus presented decomposes in the desired way into the peptidamide H-LysPhe-Phe-$NH_2$ under neutral aqueous conditions within minutes at 50° C. and about 15 min. At RT (buffer system: a,b,f,g). Thus (LA.5.2) is suitable as a linker block in the proposed way.

SYNTHESIS PATH A/EXAMPLE 6
H-Lys(Boc)-Phe-Phe-α-rac-iso-propylthio-glycyl-βAla-OH SEQ ID NO: 8 (LA.6.1)
Structure

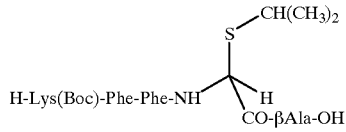

$R_1$: H-Lys(Boc)-Phe-Phe—
$R_2$: CO-βAla-OH
$R_3$: H
X: S
Y: iso-Propyl—

SYNTHESIS PATH ps $N^\alpha$-9-Fmoc-α-isopropylthio-glycin (LA.6.2)$^{(AB)}$
Empirical Formula ($C_{20}H_{21}NO_4S$)

Similarly to (LA.5.2), (LA.6.2) was obtained proceeding from (LA.1.2) by conversion with isopropylmercaptan. Yield: 613 mg (93% of th.; dichloromethane/petroleum benzine).— $^1$H-NMR (400 MHz, $CDCl_3$): δ=7.81 (d, 2H,fluorenyl-$H^1$, $^3J_{H,H}$=7.30 Hz), 7.67 (d, 2H, fluorenyl-$H^4$, $^3J_{H,H}$=7.26 Hz), 7.4 (t, 2H, fluorenyl-$H^2$, $^3J_{H,H}$=7.30 Hz), 7.25 (t, 2H, fluorenyl-$H^3$, $^3J_{H,H}$=7.30), 5.95 (d, 1H, NH), 5.47 (d, 1H, NH—C$\underline{H}$OH), 4.40 (d, 2H, CH—C$\underline{H}_2$, $^3J_{H,H}$= 6.67 Hz), 4.23 (t, 1H, C$\underline{H}$—$CH_2$, $^3J_{H,H}$=6.67 Hz), 3.11 (heptett, 1H, S—CH), 1.24 (d, 6H, S—CH$(CH_3)_2$).— $^{13}$C-NMR (75 MHz, $CDCl_3$): δ=168.9 (s, COOH), 154.7 (s, NH—COO), 143.7 (s, fluorenyl-$C_6$), 141.4 (s, fluorenyl-$C_5$), 128.2 (d, fluorenyl-$C_1$), 127.3 (d, fluorenyl-$C_4$), 124.7 (d, fluorenyl-$C_3$), 120.3 (d, fluorenyl-$H_2$), 78.9 (d, NH—$\underline{C}$HOH), 68.1 (t, CH—C$\underline{H}$2), 46.8 (d, C$\underline{H}$—$CH_2$), 34.1 (d, S—CH), 15.2 (q, $CH_3$).— MS (FAB, 3-NBA): m/z=315 (23, [M+H]$^\oplus$
H-Lys(Boc)-Phe-Phe-α-rac-iso-propylthio-glycyl-βAla-OH SEQ ID NO: 8 (LA.6.1)$^{(MV)}$
Empirical Formula ($C_{37}H_{44}N_6O_8S$)

Build-up was by common methods on an o-chlorotrityl-derivatised polystyrol resin.— MS (FAB): M/Z (3-NBA)= 732 (14, [M+H]$^\oplus$ Application Tests on the model compound (LA.6.1) are carried out in the same way as with the model compound (LA.5.1) (see above). The model compound with protected thiol function of the N.S-acetal displays, during synthesis and in tests in solution, total stability against the reagent 20% piperidine/DMF. The unprotected N.O-acetal formed after treatment with mercurous salts (see above)decomposes in aqueous, neutral solution into the desired peptidamide.

SYNTHESIS PATH A/EXAMPLE 7
H-Lys(Boc)-Phe-Phe-α-rac-tert-butylthio-glycyl-βAla-OH
SEQ ID NO: 9 (LA.7.1)
Structure

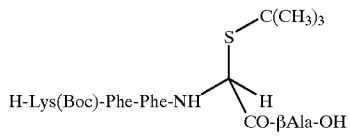

$R_1$: H-Lys(Boc)-Phe-Phe—
$R_2$: CO-βAla-OH
$R_3$: H
X: S
Y: tert-butyl

SYNTHESIS PATH $N^\alpha$-9-Fmoc-α-rac-tert-butylthio-glycine (LA.7.2)$^{(AB)}$
Empirical Formula ($C_{21}H_{23}NO_4S$)

(LA.7.2) was obtained, similarly to (LA.5.2), proceding from (LA.7.2) by conversion with tert-butylmercaptan. Yield: 612 m (92% of th.; dichloromethane/petroleum benzine).— $^1$H-NMR (400 MHz, CDCl$_3$): δ=7.81 (d, 2H,fluorenyl-H$^1$, $^3J_{H,H}$=7.30 Hz), 7.67 (d, 2H, Fluorenyl'H$^4$, $^3J_{H,H}$=7.26 Hz), 7.4 (t, 2H, fluorenyl-H$^2$, $^3J_{H,H}$=7.30 Hz), 7.25 (t, 2H, fluorenyl-H$^3$, $^3J_{H,H}$=7.30),5.95 (d,1H,NH),5.47(d, 1H, NH—C$\underline{H}$OH), 4.40 (d, 2H, CH—C $\underline{H}_2$, $^3J_{H,H}$=6.67 Hz), 4.23 (t, 1 H, C$\underline{H}$—CH$_2$), $^3J_{H,H}$=6.67 Hz), 1.25 (s, 9H, S—C(CH$_3$)$_3$).— $^{13}$C-NMR (75 MHz, CDCl$_3$): δ=168.9 (s, COOH), 154.7 (s, NH—COO), 143.7 (s, fluorenyl-C$_6$), 141.4 (s, fluorenyl-C$_5$), 128.2 (d, fluorenyl-C$_1$), 127.3 (d, fluorenyl-C$_4$), 124.7 (d, fluorenyl-C$_3$), 120.3 (d, fluorenyl-H$_2$), 78.9 (d, NH—CHOH), 68.1 (t, CH—C$\underline{H}_2$), 46.8 (d, C$\underline{H}$—CH$_2$), 37.3 (d, S-G(CH$_3$)$_3$), 15.2 (q, S—C($\underline{C}$H$_3$)$_3$).— MS (FAβ, 3-NBA): m/z=315 (23, [M+H]$^\oplus$).

H-Lys(Boc)-Phe-Phe-α-rac-tert-butylthio-glycyl-βalanin
SEQ ID NO: 10 (LA. 7.1)$^{(MV)}$
Empirical Formula ($C_{38}H_{46}N_6O_8S$)

(LA.7.1) was built up according to general peptide synthesis methods in stages, using (LA.7.2) on an o-chlorotrityl-derivatised on a polyotyrene resin.— The amino function of the protected N.S-acetal was released by treatment with 20% piperidine/DMF.— MS (FAβ): M/Z (3-NBA) 746 ([M+H]$^\oplus$).

Application

Tests on the model compound (LA.7.1) are effected in the same way as on the model compound (LA.5.1) (see above). The model compound with protected thiol function of the N.S-acetal displays, during synthesis and in tests in solution, stability against the reagent 20% piperidin/DMF.The unprotected N.O-acetal (see above), formed after treatment with mercurous salts, decomposes in an aqueous neutral solution into the desired peptidamide. The underlying N.S-acetal 15% with free thiol function can be released with the reagent trifluoromethane sulphonic acid/80% trifluoroacetic acid/2.5% TIBS/2.5% water, and chromatographically isolated (indication viaMS-FAB). The deprotected N.S-acetal decomposes by treatment with buffer system (b) and (g) within 20 min. In the desired way into the peptidamide H-Lys-Phe-Phe-NH$_2$.

Anchor Group for $N^\alpha$Boc/Bzl-Solid-Phase Peptide Synthesis

SYNTHESIS PATH A 1 EXAMPLE 8
H-Lys(Boc)-Phe-Phe-α-rac-tert-butylthio-glycyl-βAla-TentaGel SEQ ID NO: 11 (LA.8.1)
Structure

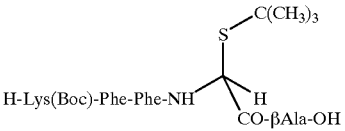

$R_1$: H-Lys(Boc)-Phe-Phe—
$R_2$: CO-βAla-OH
$R_3$: H
X: S
Y: tert-butyl

SYNTHESIS PATH $N^\alpha$-Boc-α-rac-hydroxy-glycin (LA.8.2)$^{(AB)}$
Empirical Formula ($C_{21}H_{23}NO_4S$)

Similarly to (LA.1.2), (LA.8.2) was obtained proceeding from aminoformic acid-tert-butylester by conversion with 2.5 eq. Glyoxalic acid in diethylether/THF=2:3. Yield: 87% of theoretical; white solid matter/petroleum benzine.— $^1$H-NMR (400 MHz, CDCl$_3$): δ=5.27 (s, br, 1H, NH—CH—OH), 1.41 (s, 9H, C(CH$_3$)$_3$).— $^{13}$C-NMR (100 MHz, CDCl$_3$): δ=175.5 (s, COOH), 154.7 (s, NH—COO), 81.1 (s, $\underline{C}$(CH$_3$)$_3$), 54.1 (d, NH—CH—OH), 32.2 (q, C($\underline{C}$H$_3$)$_3$).

$N^\alpha$-Boc-α-rac-tert-butylthio-glycine (LA.8.3)$^{(AB)}$
Empirical Formula ($C_{21}H_{23}NO_4S$)

Similarly to (LA.7.2), (LA.8.3) was obtained proceeding from (LA.8.2) by conversion with 4 eq. Tert-butylmercaptan in glacial acetic acid (RZ=3 d). Yield: 56% of th.; white solid matter, dichloromethane/petroleum benzine, -20° C. (14 d)).—Smp.:101° C.; $^1$H-NMR (400 MHz, CDCl$_3$): δ=5.27 (s, br, 1 H, NH—CH—OH), 1.47 (s, gH, sc(CH$_3$)$_3$), 1.41 (s, 9H, NHCOOC(CH$_3$)$_3$).— $^{13}$C-NMR (100 MHz, CDCl$_3$): δ=175.4 (s, COOH), 154.3 (s, NH—COO), 81.5 (s,$\underline{C}$(CH$_3$)), 54.1 (d, NH—CH—OH), 46.3 (s, S$\underline{C}$(CH$_3$)$_3$), 32.2 (q, C( $\underline{C}$H$_3$)$_3$), 28.1 (q, C($\underline{C}$H$_3$)$_3$).

H-Lys(Boc)-Phe-Phe-α-rac-tert-butylthio-glycyl-βAla-TentaGel SEQ ID NO: 11 (LA.8.1)$^{(MV)}$
Empirical Formula ($C_{38}H_{46}N_6O_8S$)

(LA.8.1) was built up according to the general peptide synthesis methods of Boc Boc SPPS and Fmoc SPPS in stages, using (LA.8.3) on an ethylene glycol-styrol graft polymer (TentaGel S Amine).— In addition the solid-phase carrier was functionalised with Fmoc-βAla-OH, activating with DIC/HOBt according to the methods of Fmoc SPPS, and the amino function was released with 20% piperidine (charge 0.24 mmol/g). (LA.8.3) was coupled into DMF, activating DIC/HOBt, the solid-phase carrier successively washed with DMF and DCM, and the amino function deprotected with 55% TFA/DCM (2.5% TIBS, 2.5% water) (20 min.). The solid-phase carrier is again washed with DCM and Boc-Phe-OH coupled by activating DIC/HOBt in DCM, adding 1 eq. DIEA (30 min.). The reagents are removed by washing with DCM and the amino function deprotected with 55% TFA/DCM (2.5% TIBS, 2.5% water). Renewed coupling of Boc-Phe-OH and release of the amino function are effected. Fmoc-Lys(Boc)—OH is coupled by activation of DIC/HOBt into DMF,and the charge on the carrier material determined by quantitative division from Fmoc(0.23 mmol/g). The carrier material is washed with DCM and the peptide sequence deprotected with 95% TFA/5% TFMSA (2.5% TIBS, 2.5% water). After 3 washings each with MeOH/water=1:1 (1% HCl) und 1M ACOH, the carrier material is dried in HV for 6 h and the peptide H-Lys-Phe-Phe-NH2 eluted with 10 mM $KH_2PO_4$/ $Na_2HPO_4$ (pH 7.5) at 37° C. (homogeneous according to RP-C18-HPLC and MALDI-TOF-MS (matrix sinapic acid).

SYNTHESIS PATH B/EXAMPLE 1
$N^\alpha$Ac-Phe-$\alpha$-methoxy-glycinmethylester (LB.1.1)$^{(MV)}$
Structure

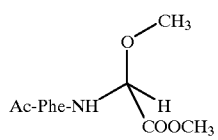

$R_1$: Ac-Phe—
$R_2$: COOCH3
$R_3$: H
X: O
Y: CH3

SYNTHESIS PATH
$N^\alpha$-Acetyl-L-phenylalanyl-$\alpha$-rac-hydroxy-glycin (LB.1.2)
Empirical Formula ($C_{13}H_{16}N_2O_5$)

103.1 mg (50 $10^{-5}$ mol) $N^\alpha$-acetyl-phenylalanylamide are stirred together with 92 mg (100 $10^{-5}$ mol) glyoxalis acid hydrate in 5 ml absolute dioxane at RT over 2 d. The reaction mixture from the diastereomeric compounds (LB.1.2) is concentrated and RP-$C_{18}$-HPLC chromatographically separated.— Yield: 131 mg (94% of th.).— $^1$H-NMR (400 MHz, $D_2O$): δ=7.40–7.15 (m,5H, phenyl-H), 5.59 (d, 1H, NH—C$\underline{H}$—OH), 4.61 (m, 1H, NH—C$\underline{H}$—CO), 3.10 (AB-q, 1H, C$\underline{H_2}$—$C_6H_5$) $^3J_{H,H}$=6.7 Hz, $^2J_{H,H}$=14.0 Hz), 2.95 (AB-q, 1H, C$\underline{H_2}$—$C_6H_5$, $^3J_{H,H}$=6.7 Hzy $^2J_{H,H}$=14.0 Hz), 2.10 (s, 3H, C$\underline{H_3}$).— $^{13}$C-NMR (75 MHz, $D_2O$):δ=174.8 (s, $CH_3$—$\underline{C}$O), 174.2 (s,$\underline{C}$OOH), 173.16/172.97$^{[dia]}$ (s, CO—NH), 137.2 (s, phenyl-H), 130.0 (d, phenyl-H), 129.5 (d, phenyl-H), 127.9 (d,phenyl-H), 123.5 (s, phenyl-H), 72.1 (d, NH—$\underline{C}$HOH), 55.8/55.7$^{[dia]}$ (d, NH—C$\underline{H}$—CO), 37.8/37.7$^{[dia]}$ (t, $\underline{C}H_2$—$C_6H_5$), 22.4 (q, $CH_3$).

$N^\alpha$-Acetyl-L-phenylalanyl-$\alpha$-rac-methoxy-glycinemethylester (LB.1.1)$^{(MV)}$
Empirical Formula ($C_{15}H_{20}N_2O_5$)

Similarly to (PA.1.3), 70.1 mg (25 10–5 mol) (LB.1.2) is converted in methanol. Yield: 65 mg (88% of th./colourless oil).—$^1$H-NMR (400 MHz, $CDCl_3$): δ=7.40–7.15 (m, 5H, phenyl-H), 5.59 (d, 1H, NH—CH—OH), 4.61 (m, 1H, NH—C$\underline{H}$—CO), 3.81 (s, 3H, $CH_3$), 3.42 (s, 3H, $CH_3$), 3.10 (AB-q, 1H, C$\underline{H_2}C_6H_5$) $^3J_{H,H}$=6.7 Hz, $^2J_{H,H}$=14.0 Hz), 2.95 (AB-q, 1H, C$\underline{H_2}$—$C_6H_5$, $^3J_{H,H}$=6.7 Hz, $^2J_{H,H}$=14.0 Hz, 2.10 (s, 3H, $CH_3$).— $^{13}$C-NMR (75 MHz, $CDCl_3$): δ=174.8 (s, $CH_3$—$\underline{C}$O), 174.2 (s, $\underline{C}$OOH), 173.16/172.97$^{[dia]}$ (s, CO—NH), 137.2 (s, phenyl-H), 130.05 (d, phenyl-H), 129.5 (d, phenyl-H), 127.5 (d, phenyl-H), 72.1 (d, NH—$\underline{C}$HOH), 55.7/55.6$^{[dia]}$ (d, NH—C$\underline{H}$—CO), 37.8/37.7$^{[dia]}$ (t, $\underline{C}H_2$—$C_6H_5$), 22.4 (q, $CH_3$).— MS (FAB): m/z=309 (15, [M+H]$^\oplus$).

Application
The stability of (LB.1.1) was tested in 20% piperidine-DMF (usual conditions of sysnthesis on $R_1$ in the course of $N^\alpha$-Fmoc/tBu-solid-phase peptide synthesis) at RT over 2 d. (LB.1.1) shows total stability under these conditions. After release of the hydroxyl function of the N.O-acetal, the reaction product is treated with buffer system (a) and (b) at RT (decomposition after 20 min.), 37° C. (decomposotion after 5 min.). In all cases the N.O-acetal with free hydroxyl function decomposes rapidly and quantitatively into the desired Ac-Phe-$NH_2$.

SYNTHESIS PATH B/EXAMPLE 2
H-Lys(Boc)-Phe-Phe-$\alpha$-rac-alkyl/arylthio-glycyl-βAla-OH
SEQ ID NO: 12 (LB.2.1)
Structure

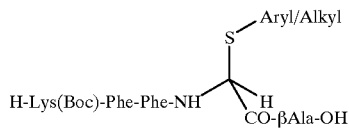

$R_1$: H-Lys(Boc)-Phe-Phe—
$R_2$: CO-βAla-OH
$R_3$: H
X: S
Y: alkyl-/aryl—

SYNTHESIS PATH
$N^\alpha$-9-Fmoc-L-phenylalaninamide (LB.2.2)
Empirical Formula ($C_{24}H_{22}N_2O_3$)

There is slowly instilled into a solution of phenylalanylamide in dioxane/10% $Na_2CO_3$ a solution of chloroformic acid-9-fluoreneylmethylester in dioxand at 0° C. The solution is stirred for a further ih at 0° C., then for a further 15 h at RT. The solid matter is suction-filtered off, wasged with water and petroleum benzine and dried in high vacuum. Yield: (98% of th.).— $^1$H-NMR (400 MHz, DMSO-$d_6$): δ=7.81 (d, 2H, fluorenyl-$H^1$, $^3J_{H,H}$=7.30 Hz),7.67 ('m', 2H, fluorenyl-$H^4$, $^3J_{H,H}$=7.26 Hz), 7.40–7.15 (m, 9H, fluorenyl-H/phenyl-H), 6.1 (d, 1H, NH), 5.5 (s (br), 2H, $NH_2$), 4.40–4.27 (m, 3H, NH—CH—CO/CH—C$\underline{H_2}$), 3.10 (AB-q, 1H, C$\underline{H_2}$—$C_6H_5$, $^3J_{H,H}$=6.7 Hz, $^2J_{H,H}$=14.0 Hz),2.95 (AB-q,1H, C$\underline{H_2}$—$C_6H_5$), $^3J_{H,H}$=6.7 Hz, $^2J_{H,H}$=14.0 Hz).— $^{13}$C-NMR (75 MHz, DMSO-$d_6$): δ=172.1 (s, CO—$NH_2$), 156.4 (s, NH—COO), 137.2 (s, phenyl-H), 130.0–120.5 (5 signals) (d, fluorenyl-H/phenyl-H), 57.1 (d, NHCH—$\underline{C}$O), 37.9 (t, $\underline{C}H_2$—$C_6H_5$).

$N^\alpha$-9-Fmoc-glycinamide (LB.2.3)
Empirical Formula ($C_{16}H_{16}N_2O_3$)

(LB.2.2) is synthesised similarly to (LB.2.2). Yield: (97% of theoretical).—1H-NMR (400 MHz, DMSO-$d_6$): δ=7.81 (d, 2H, fluorenyl-$H^1$, $^3J_{H,H}$=7.30 Hz), 7.67 (d, 2H, fluorenyl-$H^4$, $^3J_{H,H}$=7.26 Hz), 7.4 (t, 2H, fluorenyl-$H^2$, $^3J_{H,H}$=7.30 Hz), 7.25 (t,2H, fluorenyl-$H^3$, $^3J_{H,H}$=7.30), 7.2 (s (br), 1H, $NH_2$), 6.9 (t (br), 1H, CO—N$\underline{H}$), 4.35 (d, 2H, CH—C$\underline{H_2}$), $^3J_{H,H}$=6.67 Hz), 4.23 (t, 1H, C$\underline{H}$—CH2), $^3J_{H,H}$=6.67 Hz), 3.52 (d, 2H, NH—C$\underline{H_2}$—CO, $^3J_{H,H}$=7.1 Hz).—$^{13}$C-NMR (75 MHz, DMSO-$d_6$): δ=168.9 (s, COOH), 154.7 (s, NH—COO), 143.7 (s, fluorenyl-$C_6$),141.4 (s, fluorenyl-$C_5$), 128.2 (d, fluorenyl-$C_1$), 127.3 (d, fluorenyl-$C_4$), 124.7 (d, fluorenyl-$C_3$), 120.3 (d, fluorenyl-$H_2$), 78.9 (d, NH—$\underline{C}$HOH), 68.1 (t, CH—C$\underline{H_2}$), 66.2 (t, NH—$CH_2$—CO), 46.8 (d, C$\underline{H}$—$CH_2$).

$N^\alpha$-9-Fmoc-L-phenylalanyl-rac-$\alpha$-hydroxy-glycin (LB.2.4)
Empirical Formula ($C_{26}H_{24}N_2O_6$)

97 mg (25 10-5 mol) (LB.2.2) are refluxed with 92 mg (100 $10^{-5}$ mol) glyoxalic acid monohydrate in 5 ml THF over 24 h. The reaction mixture is poured into ethylacetate and extracted 3× against saturated NaCl solution. The organic phase is dried over $Na_2SO_4$, concentrated and the residue crystallised from dichloromethane/petroleum benzine. Yield: 104 mg (90% of th.— white solid matter).— $^1$H-NMR (400 Mhz, $CDCl_3$): $\delta$=7.81 (d, 2H, fluorenyl-$H^1$, $^3J_{H,H}$=7.30 Hz), 7.67 (d, 2H, fluorenyl-$H^4$,$^3J_{H,H}$=7.26 Hz), 7.40–7.15 (m, 9H, fluorenyl-H/phenyl-H), 6.1 (d, 1H, NH), 5.47 (d, 1H, NH—C$\underline{H}$—OH), 4.40–4.27 (m, 3H, NH—C$\underline{H}$—CO/CH—C$\underline{H}_2$), 4.23 (t, 1H) C$\underline{H}$—$CH_2$, $^3J_{H,H}$=6.67 Hz), 3.10 (AB-q, 1H, C$\underline{H}_2$—$C_6H_5$, $^3J_{H,H}$=6.7 Hz, $^2J_{H,H}$=14.0 Hz), 2.95 (AB-q, 1H, C$\underline{H}_2$—$C_6H_5$ $^3J_{H,H}$=6.7 Hz, $^2J_{H,H}$=14.0 Hz).— $^{13}$C-NMR (75 MHz, $CDCl_3$): $\delta$=174.4 (s, COOH), 172.1 (s, CO—$NH_2$),— 156.4 (s, NH—COO), 143.7 (s, fluorenyl-$C_6$), 141.4 (s, fluorenyl-$C_5$), 137.2 (s, phenyl-H), 130.0–120.5 (5 signals) (d, fluorenyl-H/phenyl-H), 72.1 (d, NH—$\underline{C}$HOH), 68. 1 (t, CH—C$\underline{H}_2$), 56.6/55.4$^{[dia]}$ (d, NH—$\underline{C}$H—CO), 47.3 (d, C$\underline{H}$—$CH_2$), 37.9 (t, $\underline{C}H_2$—$C_6H_5$).— MS (FAB, thioglycerin): m/z=461 (15, [M+H]$^\oplus$).

$N^\alpha$-9-Fmoc-glycyl-rac-$\alpha$-hydroxy-glycin (LB.2.5)
Empirical Formula ($C_{19}H_{18}N_2O_6$)

(LB.2.5) is synthesised similarly to(LB.2.4). Yield: 64 mg (68% of th. -White solid matter).— $^1$H-NMR (300 MHz, $CDCl_3$): $\delta$=7.81 (d, 2H, fluorenyl-$H^1$, $^3J_{H,H}$=7.30 Hz), 7.67 (d, 2H, fluorenyl-$H^4$, $^3J_{H,H}$=7.26 Hz), 7.4 (t, 2H, fluorenyl-$H^2$,$^3J_{H,H}$=7.30 Hz), 7.25 (t,2H, fluorenyl-$H^3$, $^3J_{H,H}$=7.30), 5.90 (t(br), 1H, CO—N$\underline{H}$), 4.35 (d, 2H, CH—C$\underline{H}_2$), $^3J_{H,H}$=6.67 Hz), 4.23 (t, 1 H, C$\underline{H}$—$CH_2$), $^3J_{H,H}$=6.67 Hz), 3.52 (d, 2H, NH—C$\underline{H}_2$—CO, $^3J_{H,H}$=7.1 Hz).— $^{13}$C-NMR (75 MHz, $CDCl_3$): $\delta$=171.4 (s, COOH), 168.9 (s, CONH), 154.7 (s, NH—COO), 143.7 (s, fluorenyl-$C_6$), 141.4 (s, fluorenyl-C5), 128.2 (d, fluorenyl-$C_1$), 127.3 (d, fluorenyl-$C_4$), 124.7 (d, fluorenyl-$C_3$), 120.3 (d, fluorenyl-$H_2$), 77.4 (d, NH—$\underline{C}$HOH), 68.1 (t, CH—C$\underline{H}_2$), 66.2 (t, NH—$CH_2$—CO), 46.8 (d, C$\underline{H}$—$CH_2$).— MS (FAB, 3-NBA): m/z=271 (5, [M+H]$^\oplus$).

$N^\alpha$-9-Fmoc-L-phenylalanyl-rac-$\alpha$-hydroxy-glycine benzylester (LB.2.6)
Emnpirical Formula ($C_{21}H_{23}NO_4S$)

Similarly to (LA.1.3), (LB.2.6) is synthesised by direct conversion of (1) with benzyl bromide and caesium carbonate in DMF. Yield: 64% of th.— white solid matter.— $^1$H-NMR (400 MHz, $CDCl_3$): $\delta$=7.81 (d, 2H, fluorenyl-$H^1$, $^3J_{H,H}$=7.30 Hz), 7.67 (d,2H, fluorenyl-$H^4$, $^3J_{H,H}$=7.26 Hz), 7.40–7.15 (m, 14H, fluorenyl-H/phenyl-H), 6.1 (d, 1 H, NH), 5.47 (d, 1H, NH—C$\underline{H}$—OH), 5.23 ('d', 2H COOC$\underline{H}$2), 4.40–4.27 (m, 3H, NH—C$\underline{H}$—CO/CH—C$\underline{H}_2$), 3.10 (AB-q, 1H, C$\underline{H}_2$—$C_6H_5$, $^3J_{H,H}$=6.7 Hz, $^2J_{H,H}$=14.0 Hz), 2.95 (AB-q, 1H, C$\underline{H}_2$—$C_6H_5$, $^3J_{HH}$ =6.7 Hz, $^2J_{H,H}$=14.0 Hz).— $^{13}$C-NMR (75 MHz, $CDCl_3$): $\delta$=174.4 (s, COOH), 172.1 (s, CO—$NH_2$), 156.4 (s, NH—COO), 143.7 (s, fluorenyl-$C_6$), 141.4 (s, fluorenyl-$C_5$), 137.2 (s, phenyl-H), 135.2(s,phenyl-H),130.0–120.5 (8 signals/partly Split$^{[dia]}$ (d, fluorenyl-H/phenyl-H), 72.1 (d, NH—$\underline{C}$HOH), 68.1 (t, CH—C$\underline{H}_2$), 67.5 (t, COO—C$\underline{H}_2$), 56.6/55.4$^{[dia]}$ (d, NH—C$\underline{H}$—C$\overline{O}$), 47.3 (d, C$\underline{H}$—$CH_2$), 37.9 (t, $\underline{C}H_2$—$C_6H_5$).— MS (FAB, thioglycerin) m/z=461 (15, [M+H]$^\oplus$).

The alkyl-/aryl thio compounds were obtained, similarly to (LA.5.2) from (LB.2.4) and the corresponding thiols. The data are reproduced in the following. The compounds behave similarly to (LA.5.2-LA.7.2). By means of treatment with Hg-II salts, the corresponding model compounds transform into the corresponding N.O-acetals. By means of 95% TFA/2.5% TIBS/2.5% water, (LB.2.9) can be transferred directly into the corresponding deprotected N.S-acetal (fre thiol function). This decomposes in the desired way into the peptidamide H-Lys-Phe-Phe-NH2.

$N^\alpha$-9-Fmoc-L-phenylalanyl-rac-$\alpha$-isopropylthio-glycine (LB.2.7)$^{(AB)}$ Empirical Formula ($C_{21}H_{23}NO_4S$)

Yield: 90% of th..— $^1$H-NMR (400 MHz, $CDCl_3$): $\delta$=7.81 (d, 2H, fluorenyl-$H^1$, $^3J_{H,H}$=7.30 Hz), 7.67 (d, 2H, fluorenyl-$H^4$, $^3J_{H,H}$=7.26 Hz), 7.40–7.15 (m, 9H, fluorenyl-H/phenyl-H), 6.1 (d, 1H, NH), 4.95 (d, 1H, NH—C$\underline{H}$—S), 4.40–4.27 (m, 3H, NH—C$\underline{H}$—CO/CH—C$\underline{H}_2$), 4.20 (t, 1H, C$\underline{H}$—$CH_2$, $^3J_{H,H}$=6.70 Hz), 3.22 (heptet, 1H, S—CH, $^3J_{H,H}$=6.74 Hz), 3.10 (AB-q, 1H, C$\underline{H}_2$—$C_6H_5$, $^3J_{H,H}$=6.7 Hz, $^2J_{H,H}$=14.0 Hz), 2.95 (AB-q, 1H, C$\underline{H}_2$—$C_6H_5$, $^3J_{H,H}$=6.7 Hz, $^2J_{H,H}$=14.0 Hz),1.20(d,6H, S—C$\overline{H}$($CH_3$)$_2$, $^3J_{H,H}$=6.74 Hz).— $^{13}$C-NMR (75 MHz, $CDCl_3$): $\delta$=174.4 (s, COOH), 172.1 (s, CO—$NH_2$), 156.4 (s, NH—COO), 143.7 (s, fluorenyl-$C_6$), 141.4 (s, fluorenyl-$C_5$), 137.2 (s, phenyl-H), 130.0–120.5 (5 signals) (d, fluorenyl-H/phenyl-H), 72.1 (d, NH—$\underline{C}$HOH), 68.1 (t, CH—C$\underline{H}$2), 56.6/55.4$^{[dia]}$ (d, NH—C$\underline{H}$—CO), 47.3 (d, C$\underline{H}$—$CH_2$), 37.9 (t,$\underline{C}H_2$—$C_6H_5$), 34.1 (d, S—CH), 15.2 (q,$CH_3$).— MS (FAB, thioglycerin): m/z=461 (15, [M+H]$^\oplus$).

$N^\alpha$-9-Fmoc-L-phenylalanyl-rac-$\alpha$-benzylthio-glycine (LB.2.8)$^{(AB)}$ Empirical Formula ($C_{33}H_{30}N_2O_5S$)

Yield: 90% of th.— $^1$H-NMR (400 MHz, $CDCl_3$): $\delta$=7.81 (d, 2H) fluorenyl-$H^1$, $^3J_{H,H}$=7.30 Hz),7.67(d, 2H, fluorenyl-$H^4$, $^3J_{H,H}$=7.26 Hz), 7.40–7.00 (m, 14H, fluorenyl-H/phenyl-H), 6.1 (d, 1 H, NH), 4.85 (d, 1 H, NH—C$\underline{H}$—OH), 4.40–4.27 (m, 3H, NH—C$\underline{H}$— CO/CH—$CH_2$), 4.15 (t, 1H, C$\underline{H}$—$CH_2$, $^3J_{H,H}$=6.70 Hz), 3.73$^{[dia]}$ ('d', 2H, S—C$\underline{H}_2$—$C_6H_5$), 3.00 (m, 2H, C$\underline{H}$2—$C_6H_5$).— $^{13}$C-NMR (75 MHz, $CDCl_3$): $\delta$=174.4 (s, COOH), 170.8/170.6$^{[dia]}$ (S, CO—NH), 156.4 (s, NH—COO), 143.7 (s, fluorenyl-$C_6$), 141.4 (s, fluorenyl-$C_5$), 137.2 (s, phenyl-H), 135.9/135.8$^{[dia]}$ (s, phenyl-H), 130.0–120.5$^{[dia]}$ (14 signals) (d, fluorenyl-H/phenyl-H), 7.6/67.3$^{[dia]}$ (t, CHC$\underline{H}_2$), 56.8/55$^{[dia]}$ (d,NH—C$\underline{H}$—S) 53.7/53.3$^{[dia]}$ (NH—C$\underline{H}$—CO), 47.3 (d, C$\underline{H}$—$CH_2$), 39.0/38.2$^{[dia]}$ (t, $\underline{C}H_2$—$C_6H_5$),35.4 (t, S—$\underline{C}H_2$—$C_6H_5$).

$N^\alpha$-9-Fmoc-L-phenylalanyl-rac-$\alpha$-triphenylmethylthio-glycine (LB.2.9)$^{(AB)}$ Empirical Formula ($C_{45}H_{38}N_2O_5S$)

Yield: 45% of th.— $^1$H-NMR (400 MHz, $CDCl_3$): $\delta$=7.81 (d, 2H, fluorenyl-$H^1$, $^3J_{H,H}$=7.30 Hz), 7.67 ('dd', 2H, fluorenyl-$H^4$,$^3J_{H,H}$=7.26 Hz), 7.50–7.00 (m, 24H, fluorenyl-H/phenyl-H/trityl-H), 4.95 (d, 1 H, NH—C$\underline{H}$—S), 4.40–4.27 (m, 3H, NH—C$\underline{H}$—CO/CH—C$\underline{H}_2$), 4.15 (t, 1H, C$\underline{H}$—$CH_2$, $^3J_{H,H}$=6.70 Hz), 3.10 (m, 2H, C$\underline{H}_2$—$C_6H_5$),.— $^{13}$C-NMR (75 MHz, $CDCl_3$): $\delta$=174.4 (s, COOH), 172.1 (s, CO—$NH_2$), 156.4 (s, NH—COO), 143.7 (s, fluorenyl-$C_6$), 141.4 (s, fluorenyl-$C_5$), 137.2 (s, phenyl-H), 134.7 (s, trityl-H), 130.0–120.5 (8 signals) (d, fluorenyl-C/phenyl-C/trityl-C), 68.1 (t, CH—C$\underline{H}_2$), 56.6/55.4$^{[dia]}$ (d, NH—C$\underline{H}$—CO), 53.8/53.5$^{[dia]}$ (d, NH—C$\underline{H}$—S) 47.3 (d, C$\underline{H}$—$CH_2$), 37.9 (t, $\underline{C}H$ $_2$—$C_6H_5$), 36.0 (t, S—$\underline{C}$($C_6H_5$)3).—MS (FAB, thioglycerin): m/z 719 (15, [M+H]$^\oplus$).

SYNTHESIS PATH B 1 EXAMPLE 3
H-Lys(Boc)-Phe-Phe-α-rac-(methoxymethyl)oxyglycyl-βAla-OH SEQ ID NO: 13 (LB.3.1)
Structure

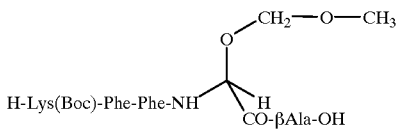

R$_1$: H-Lys(Boc)-Phe-Phe—
R$_2$: CO-βAla-OH
R$_3$: H
X: O
Y: CH$_3$OCH$_2$

SYNTHESIS PATH
N$^\alpha$,-9-Fmoc-L-phenylalanyl-rac-α-(methoxymethyl)oxy-glycine (LB.3.2)$^{(AB)}$
Empirical Formula (C$_{21}$H$_{23}$NO$_4$S)

(LB.3.2) is synthesized, similarly to (LB.3.4), by conversion of (LB.2.4) with formaldehyde dimethylacetal. Yield: 67% of th.— $^1$H-NMR (400 Mhz, CDCl$_3$): δ=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.40–7.15 (m, 9H, fluorenyl-H/phenyl-H), 6.5(d,1H, NH), 6.1 (d, 1H, NH), 5.47 (d, IH, NH—CH—O), 5.00 (d, 1H, O—CH$_2$—O, $^2J_{H,H}$=7.30 Hz), 4.90 (d, 1H, O—CH$_2$—O, $^2J_{H,H}$=7.30 Hz), 4.40–4.27 (m, 3H, NH—CH—CO/CH—CH$_2$), 4.15 (t, 1 H, CH—CH$_2$), $^3J_{H,H}$=6.70 Hz),3.45 (s, 3H, CH$_3$O), 3.10 (m, 1H, CH$_2$—C$_6$H$_5$).— $^{13}$C-NMR (75 MHz, CDCl$_3$): δ=174.4 (s, COOH), 172.1 (s, CO—NH$_2$), 156.4 (s, NH—COO), 143.7 (s, fluorenyl-C$_6$), 141.4 (s, fluorenyl-C$_5$), 137.2 (s, phenyl-H), 130.0–120.5 (5 signals) (d, fluorenyl-H/phenyl-H), 77.0 (t, O—CH$_2$—O), 72.1 (d, NH—CHO), 68.1 (t, CH—CH$_2$), 56.6/55.4$^{[dia]}$ (d, NH—CH—CO), 51.6 (q, CH$_3$O), 47.3 (d, CH—CH$_2$)—MS (FAB, thioglycerin): m/z=461 (15, [M+H]$^\oplus$).

H-Lys(Boc)-Phe-Phe-α-rac-(methoxymethyl)oxyglycyl-βAla-OH SEQ ID NO: 13 (LB.3.1)$^{(MV)}$
Empirical Formula (C$_{36}$H$_{42}$N$_6$O$_{10}$)

(LA.3.1) is built up according to general peptide synthesis methods on an o-chlorotrityl-functionalized resin, and detached as a protected peptide according to known methods.— MS (FAB): M/Z (3-NBA)=718 ([M+H]$^\oplus$).

FURTHER EXAMPLES

In addition to (LB.3.2), further bi- and trifunctional amino acids, in the form of their amides, protected in the side chain and commercially accessible, were converted to the corresponding anchor blocks with MOM protected N.O-acetal. The reaction sequence corresponds to (LB.3.2). The acid-labile side chain functions are stable under the acidic conditions for introduction of the N,OR-acetalic anchor grouping. The following were synthesised:

N$^\alpha$9-Fmoc-L-Ile-rac-α-(methoxymethyl)oxy-glycine (branched bifunctional AS)
N$^\alpha$-9-Fmoc-D-Thr(tBu)-rac-α-methoxymethyl)oxy-glycine (alcohol function)
N$^\alpha$-9-Fmoc -L-Glu(tBu)-rac-α-(methoxymethyl)oxy-glycine (carboxylate function)
N$^\alpha$-9-Fmoc -L-Cys(Trt)-rac-α-(methoxymethyl)oxy-glycine (thiol function)
N$^\alpha$-9-Fmoc-L-Lys (Boc) -rac-α-(methoxymethyl)oxy-glycine (primary amine)

The experimental data for N$^\alpha$-9-Fmoc-DThr(tBu)-rac-α-(methoxymethyl)oxy-glycine are given here by way of example.

N$^\alpha$-9-Fmoc-D-Thr(tBu)-NH2 (LB.3.3)
Empirical Formula (C$_{23}$H$_{28}$N$_2$O$_4$)

(LB.3.3) is synthesized similarly to (LB.2.2). Yield: 68% of th.— white solid matter_.—$^1$H-NMR (300 MHz, CDCl$_3$): δ=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.4 (t, 2H, fluorenyl-H$^2$, $^3J_{H,H}$=7.30 Hz, 7.25 (t, 2H, fluorenyl-H$^3$, $^3J_{H,H}$=7.30), 5.90 (t (br), 1H, CO—NH), 4,35 (d, 2H, CH—CH$_2$), $^3J_{H,H}$=6.67 Hz), 4.28 (q, 1H, CH$_3$—CHOH, $^3J_{H,H}$=6.67 Hz) 4.23 (t, 1H, CH—CH$_2$, $^3J_{H,H}$=6.67 Hz), 3.58 (d, 1H, NH—CH—CO, $^3J_{H,H}$=7.1 Hz), 1.35 (d, 3H, CH$_3$—CHOH, $^3J_{H,H}$=6.67 Hz), 1.23 (s, 9H, C(CH$_3$)$_3$).—$^{13}$C-NMR (75 Mhz, CDCl$_3$): δ=176.2 (s, COOH), 168.9 (s, CONH), 154.7 (s, NH—COO), 143.7 (s, fluorenyl-C$^6$), 141.4 (s, fluorenyl-C$^5$), 128.2 (d, fluorenyl-C$_1$), 127.3 (d, fluorenyl-C$_4$), 124.7 (d, fluorenyl-C$_3$), 120.3 (d, fluorenyl-H$_2$), 74.6 (s, c(CH$_3$)$_3$), 68.1 (t, CH—CH$_2$), 67.4 (d, CH$_3$—CHOH), 62.2 (t, NH—CH—CO), 46.8 (d, CH—CH$_2$), 28.2 (q, C(CH$_3$)$_3$), 20.4 (q, CH$_3$—CHOH).— MS (FAB, 3-NBA): m/z=271 (5, [M+H]$^\oplus$ N$^\alpha$-9-Fmoc-D-Thr(tBu)-rac-α-hydroxy-glycin (LB.3.4)
Empirical Formula (C$_{25}$H$_{30}$N$_2$O$_7$)

(LB.3.4) is synthesized similarly to (LB.2.3). Yield: (98% of th.; white solid matter).— $^1$H-NMR (300 MHz, CDCl$_3$): δ=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.4 (t, 2H, fluorenyl-H$^2$, $^3J_{H,H}$=7.30 Hz), 7.25 (t, 2H, fluorenyl-H$^3$, $^3J_{H,H}$=7.30), 5.90 (t (br), 1H, CO—NH), 4.35 (d, 2H, CH—CH2), $^3J_{H,H}$=6.67 Hz), 4.28 (q, 1 H, CH$_3$—CHOH, $^3J_{H,H}$=6.67 Hz) 4.23 (t, 1H, CH—CH2, $^3J_{H,H}$=6.67 Hz), 3.58 (d, 2H, NH—CH—CO, $^3J_{H,H}$=7.1 Hz), 1.35 (d, 3H, CH$_3$—CHOH, $^3J_{H,H}$=6.67 Hz).—$^{13}$C-NMR (75 MHz, CDCl$_3$): δ=176.2 (s, COOH), 168.9 (s, CONH), 154.7 (s, NH—COO), 143.7 (s, fluorenyl-C$_6$), 141.4 (s, fluorenyl-C$_5$), 128.2 (d, fluorenyl-C$_1$), 127.3 (d, fluorenyl-C$_4$), 124.7 (d, fluorenyl-C$_3$), 120.3 (d, fluorenyl-H$_2$), 77.4 (d, NH—CHOH), 74.6 (s, C(CH$_3$)$_3$), 68.1 (t, CH—CH2), 67.4 (d, CH$_3$—CHOH), 62.2 (t, NH—CH—CO), 46.8 (d, CH—CH2), 28.2 (q, C(CH$_3$)$_3$), 20.4 (q, CH$_3$—CHOH).— MS (FAB, 3-NBA): m/z=271 (5, [M+H]$^\oplus$).

N$^\alpha$-9-Fmoc-D-Thr(tBu)-rac-α-(methoxymethyl)oxy-glycine (LB.3.5)
Empirical Formula (C$_{27}$H$_{34}$N$_2$O$_8$)

(79) is synthesized similarly to (76). Yield: (86% of th.— white solid matter).— $^1$H-NMR (300 MHz, CDCl3): 5=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.4 (t, 2H, fluorenyl-H$^2$, $^3J_{H,H}$=7.30 Hz), 7.25 (t, 2H, fluorenyl-H$^3$, $^3J_{H,H}$=7.30 Hz), 5.90 (t (br), 1H, CO—NH), 5.00 (d, 1H, O—CH$_2$—O, $^2J_{H,H}$=7.30 Hz), 4.90 (d, 1H, O—CH$_2$—O, $^2J_{H,H}$=7.30 Hz), 4.35 (d, 2H, CH—CH$_2$), $^3J_{H,H}$=6.67 Hz), 4.28 (q, 1H, CH$_3$—CHOH, $^3J_{H,H}$=6.67 Hz), 6.23 (t, 1H, CH—CH$_2$, $^3J_{H,H}$=6.67 Hz), 3.58 (d, 2H, NH—CH—CO, $^3J_{H,H}$=7.1 Hz), 3.45 (s, 3H, CH$_3$O), 1.35 (d, 3H, CH$_3$—CHOH, $^3J_{H,H}$=6.67 Hz).— $^{13}$C-NMR (75 MHz, CDCl$_3$): δ=176.2 (s, COOH), 168.9 (s, CONH), 154.7 (s, NH—COO), 143.7 (s, fluorenyl-C$_6$), 141.4 (s, fluorenyl-c$_5$), 128.2 (d, fluorenyl-C$_1$), 127.3 (d, fluorenyl-C$_4$), 124.7 (d, fluorenyl-C$_3$), 120.3 (d, fluorenyl-H$_2$), 77.4 (d, NH—CHOH), 77.0 (t, O—CH$_2$—O), 68.1 (t, CH—CH$_2$),67.4 (d, CH$_3$—CHOH), 62.2 (t, NH—CH—CO), 51.6 (q, CH$_3$O), 46.8 (d, CH—CH$_2$), 20.4 (q, CH$_3$—CHOH).— MS (FAB, 3-NBA): m/z=271 (5, [M+H]$^\oplus$).

Application

The protected peptide (LA.3.1) is treated in solution in addition with 20% piperidine/DMF over 5 h at RT. No alteration in the educt is observed (HPLC analysis). Treatment with 95% TFA/2.5% TIBS/2.5% water leads to simultaneous deprotection of BOC in the lysyl residue, and the hydroxyl function of the N.O-acetal. This deprotected peptide decomposes in the desired way into the peptidamide by treatment with buffer system (a) to (9). Reaction takes place within 15 min. At 50° C.

SYNTHESIS PATH B/EXAMPLE 4
H-Lys(Boc)-Phe-Phe-α-rac-(SEM)oxyglycyl-βAla-OH
SEQ ID NO: 14 (LB.4.1)
Structure

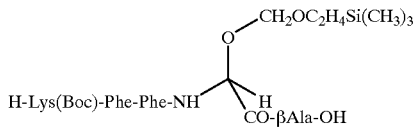

$R_1$: H-Lys(Boc)-Phe-Phe—
$R_2$: CO-βAla-OH
$R_3$: H
Y: $(CH_3)_3SiCH_2$—$CH_2$—O—$CH_2$—

SYNTHESIS PATH
$N^\alpha$-9-Fmoc-L-Phe-rac-α-(SEM)oxy-glycinebenzylester (LB.4.2)
Empirical Formula ($C_{39}H_{44}N_2O_7Si$)

Similarly to (LA.3.5), (LB.4.2) is synthesized in DMF by reaction with an excess of 2 eq. trimethylsilylethoxymethylchloride. Isolation is effected RP-$C_{18}$-HPLC chromatographically.— Yield: 60.45 mg (70% of th.).—$^1$H-NMR (400 MHz, $CDCl_3$): δ=7.81 (d, 2H, fluorenyl-$H^1$ 3$J_{H,H}$=7.30 Hz),7.67 (d, 2H, fluorenyl-$H^4$, $^3J_{H,H}$=7.26 Hz), 7.40–7.15 (m, 14H, fluorenyl-H/phenyl-H), 6.1 (d, 1H, NH), 5.47 (d, 1H, NH—C$\underline{H}$—O), 5.24 ('d', 2H, COOC$\underline{H}$2), 4.94 (d, 1 H, O—$CH_2$—O, $^2J_{H,H}$=7.20 Hz), 4.75 (d, 1 H, O—$CH_2$—O, $^2J_{H,H}$=7.20 Hz), 4.40–4.27 (m, 3H, NH–C$\underline{H}$—CO/CH—C$\underline{H}$2), 4.15 (t, 1H, C$\underline{H}$—$CH_2$), $^3J_{H,H}$=6.70 Hz), 3.82 (AB-t, 4H, C$\underline{H}$2—C$\underline{H}$2), 3.0 (m, 1H, C$\underline{H}$2—$CH6H_5$), 0.1 (S,3H, $Si(CH_3)_3$).— $^{13}$C-NMR (75 MHz, $CDCl_3$): δ=174.4 (s, COO), 172.1 (s, CO—$NH_2$), 156.4 (s, NH—COO), 143.7 (s, fluorenyl-$C_6$),141.4 (s, fluorenyl-$C_5$), 137.2 (s, phenyl-H), 134.4 (s, phenyl-H), 130.0–120.5 (8 Signale) (d, fluorenyl-H/phenyl-H), 77.0 (t, O—$CH_2$—O), 72.1 (d, NH—$\underline{C}$HO), 68.1 (t, CH—C$\underline{H}$2), 67.4 (t,$\underline{C}H_2$—$CH_2$), 67.2 (t, COO—$CH_2$), 56.6/55.4$^{[dia]}$ (d, NH—C$\underline{H}$—CO), 47.3 (d, C$\underline{H}$—$CH_2$), 37.9 (t,$\underline{C}H_2$—$C_6H_5$), 2.0 (q, $Si(CH_3)_3$).

$N^\alpha$-9-Fmoc-L-phenylalanyl-α-(trimethylilylethoxymethyl) oxy-glycine (LB.4.3)$^{(AB)}$
Empirical Formula ($C_{21}H_{23}NO_4S$)

Similarly to (LA.1.5), (LB.4.3) is synthesized from (LB.4.2) .— $^1$H-NMR (400 MHz,$CDCl_3$): δ=7.81 (d, 2H, fluorenyl-$H^1$, $^3J_{H,H}$=7.30 Hz), 7.67 (d, 2H,fluorenyl-$H^4$, $^3J_{H,H}$=7.26 Hz), 7.40–7.15 (m, 14H, fluorenyl-H/phenyl-H), 6.1 (d, 1H, NH), 5.47 (d, 1H, NH—C$\underline{H}$—O), 4.94 (d, 1H, O—$CH_2$—O, $^2J_{H,H}$=7.20 Hz), 4.75 (d, 1 H, O—$CH_2$—O, $^2J_{H,H}$=7.20 Hz), 4.40–4.27 (m, 3H, NH—C$\underline{H}$—CO/CH—C$\underline{H}$2), 4.15 (t, 1 H, C$\underline{H}$—$CH_2$) $^3J_{H,H}$=6.70 Hz), 3.82 (AB-t, 4H, C$\underline{H}$2—C$\underline{H}$2), 3.0(m, 1H, C$\underline{H}$2—$C_6H_5$), 0.1 (s, 3H, $SI(CH_3)_3O$.—$^{13}$C-NMR (75 MHz, $CDCl_3$): δ=174.4 (s, COOH), 172.1 (s, CO—NH2), 156.4 (s, NH—COO), 143.7 (s, fluorenyl-$C_6$), 141.4 (s, fluorenyl-$C_5$), 137.2 (s, phenyl-H), 134.4 (s, pheny/H), 130.0–120.5 (8 signals) (d, fluorenyl-H/phenyl-H), 77.0 (t, O—$CH_2$—O), 72.1 (d, NH—$\underline{C}$HO), 68.1 (t, CH—C$\underline{H}$2), 67.4 (t,$\underline{C}H_2$—$CH_2$), 56.6/ 55.4$^{[dia]}$ (d, NH—C$\underline{H}$—CO), 47.3 (d, C$\underline{H}$—$CH_2$), 37.9 (t, $\underline{C}H_2$—$C_6H_5$), 2.0 (q, $Si(CH_3)_3$).— MS (FAB, thioglycerin): m/z=461 (15, $[M+H]^\oplus$).

H-Lys(Boc)-Phe-Phe-α-rac-(SEM)oxyglycyl-βalanin (LB.4.1)$^{(MV)}$
Empirical Formula ($C_{21}H_{23}NO_4Si$)

According to general peptide synthesis methods, (LB.4.1) is built up on an o-chlorotrityl-functionalized resin, and detached as a protected peptide according to known methods.— MS (FAB): M/Z (3-NBA)=157 ([M+H]$^\oplus$).

Application

Treatment with 95% TFA/2.5% TIBS/2.5% water leads to simultaneous deprotection of BOC in the lysyl residue and the hydroxyl function of the N.O-acetal. This deprotected peptide decomposes in the desired way into the peptidamide by treatment with buffer system (a) to (g). Reaction takes place within 15 min. At 50° C.

In addition to the protected peptide (LB.4.1), a model compound (LB.4.4) is synthesized on the o-chlorotrityl-functionalized polystyrol resin, and divided off as a protected peptide from the resin. This protected peptide is treated with 0.2 M tetrabutylammonium fluoride/acetonitrile over 5 h. In this way the hydroxyl function od the N.O-acetal is selectively deprotected. The treatment with buffer system (g) in mixture with 35% ethanol leads to the protected peptidamide H-Lys(Boc)-Trp(Boc)-Asp(tBu)-Asn(Trt)-Phe-NH2 SEQ ID NO: 15.

H-K(Boc)-W(Boc)-D(tBu)-N(Trt)-F-α-rac-(SEM) oxyglycyl-βAla-OH (LB.4.4)
Empirical Formula ($C_{21}H_{23}NO_4Si$)
MS (FAB): M/Z (3-NBA)=1557 ([M+H]$^\oplus$).

SYNTHESIS PATH B/EXAMPLE 5
H-Lys(Boc)-Phe-Phe-α-rac-tert-butoxy-glycyl-βAla-OH
SEQ ID NO: 1 (LB.5.1)
Structure

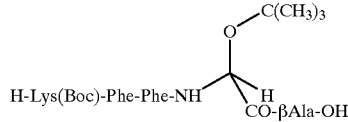

$R_1$: H-Lys(Boc)-Phe-Phe—
$R_2$: CO-βAla-OH
$R_3$: H
X: O
Y: tert-butyl

SYNTHESIS PATH
$N^\alpha$-9-Fmoc-phenylalanyl-α-rac-tert-butoxy-glycinbenzylester (LB.5.2)
Empirical Formula ($C_{28}H_{29}NO_5$)

110 mg (25 10$^{-5}$ mol) (LB.2.4) are converted under reflux in 2 ml absolte THF with 55 μl dist. (75 10$^{-5}$ mol) thionyl chloride over 1 h. The reaction mixture is completely concentrated and briefly treated in HV. 2 ml absolute tert-butanol and 42 μl (25 10$^{-5}$ mol) ethyldiisopropylamine are added and refluxed for 2 h. The reaction mixture is poured into a saturated aqueous NaCl solution and the aqueous phase extracted 2× with 100 ml ethyl acetate. The organic phase is dried over $MgSO_4$ and concentrated (LB.5.2) is either RP-$C_{18}$-HPLC chromatographically cleaned to homogeneity.— 1 H-NMR (400 MHz, $CDCl_3$): δ=7.81(d, 2H, fluorenyl-$H^1$, $^3J_{H,H}$=7.30 Hz), 7.67 (d, 2H, fluorenyl-$H^4$, $^3J_{H,H}$=7.26 Hz), 7.40–7.15 (m, 14H, fluorenyl-H/phenyl-H), 6.1 (d, 1H, NH), 5.47 (d, 1H, NH—CH—OH), 5.23 ('d', 2H COOCH$_2$), 4.40–4.27 (m, 3H, NH—CH—CO/CH—CH$_2$), 4.15 (t, 1H, CH—CH$_2$), $^3J_{H,H}$=6.70 Hz), 3.0 (m, 2H, CH$_2$—C$_6$H$_5$), 1.25 (s, 9H,C(CH$_3$)$_3$).— $^{13}$C-NMR (75 MHz, CDCl$_3$): δ=174.4 (s, COO), 172.1 (s, CO—NH$_2$), 156.4 (s, NH—COO), 143.7 (s, fluorenyl-C$_6$), 141.4 (s, fluorenyl-C$_5$), 137.2 (s, phenyl-H), 135.2 (s, phenyl-H), 130.0–120.5 (8 signals/partly split$^{[dia]}$] (d, fluorenyl-H/phenyl-H), 74.6 (s, C(CH$_3$)$_3$), 72.1 (d, NH—CHOH), 68.1 (t, CH—CH$_2$), 67.5 (t, COO—CH$_2$), 56.6/55.4$^{[dia]}$ (d, NH—CH—CO), 47.3 (d, CH—CH$_2$), 37.9 (t,CH$_2$—C$_6$H$_5$), 28.2 (q, C(CH$_3$)$_3$)— MS (FAB, thioglycerin): m/z=461 (15, [M+H]$^⊕$).

N$^α$-9-Fmoc-phenylalanyl-α-rac-tert-butoxy-glycine (LB.5.3)$^{(AB)}$

Empirical Formula (C$_{19}$H$_{23}$NO$_5$)

115 mg (25 10$^{-5}$ mol) (LB.5.2) are dissolved in 3 ml abs. Ethanol/ethyl acetate. A spatula tip of palladium/activated carbon (Fluka) is added and hydrogen is passed through the solution for 25 min. The catalyst is filtered off and (LB.5.3) is RPC$_{18}$-HPLC chromatographically isolated. Yield: 60.45 mg (70% of th.).— $^1$H-NMR (400 MHz, CDCl$_3$): δ=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.40–7.16 (m,9H, fluorenyl-H/phenyl-H), 6.1 (d, 1 H, NH), 5.47 (d, 1 H, NH—CH—OH), 4.40–4.27 (m, 3H, NH—CH—CO/CH—CH2), 4.15 (t, 1H, CH—CH$_2$, $^3J_{H,H}$=6.70 Hz), 3.0 (m, 2H, CH$_2$C$_6$H$_5$), 1.25 (s, 9H, C(CH$_3$)$_3$).— $^{13}$C-NMR (75 MHz, CDCl$_3$): δ=174.4 (s, COOH), 172.1 (s, CO—NH$_2$), 156.4 (s, NH—COO), 143.7 (s, fluorenyl-C$_6$), 141.4 (s, fluorenyl-C$_5$), 137.2 (s, phenyl-H), 135.2 (s, phenyl-H), 130.0–120.5 (5 signals/partly divided $^{[dia]}$) (d, fluorenyl-H/phenyl-H), 74.6 (s, C(CH$_3$)$_3$), 72.1 (d, NH—CHOH), 68.1 (t, CH—CH$_2$), 56.6/55.4$^{[dia]}$ (d, NH—CH—CO), 47.3 (d, CH—CH$_2$), 28.2 (q, C(CH$_3$)$_3$).

H-Lys(Boc)-Phe-Phe-α-rac-tert-butoxy-glycyl-βAla SEQ ID NO: 16 (LB.5.1)$^{(MV)}$ Empirical Formula (C$_{38}$H$_{46}$N6O$_9$)

The protected peptide (LB.5.1)is built up according to usual conditions on an o-chlorotrityl-functionalized resin, using (LB.5.2), and is divided off from the carrier. The NH$_2$.OR-acetal is relased with 20% piperidine/DMF.— MS (FAB, thioglycerin): m/z=731 (15, [M+H]$^⊕$).

Application

The protected peptide (LB.5.1) dispplays total stability against 20% piperidine/DMF (shown by quantitative UV/VIS analysis of the individual coupling steps protected peptide in solution with the abovenamed reagent). After splitting of the hydroxyl protective group according to normal procedures (and simultaneously by Boc in the lysyl residue), the deprotected peptide is treated with buffer system (a), (b) and (g). The model compound (LB.5.1) decomposes in the desired way into the peptidamide H-Lys-Phe-Phe-NH$_2$.

SYNTHESIS PATH B/EXAMPLE 6

H-Lys(Boc)-Phe-Phe-α-rac-methoxyglycyl-βAla-OH SEQ ID NO: 17 (LB.6.1)

Structure

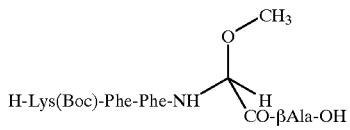

R$_1$: H-Lys(Boc)-Phe-Phe—
R$_2$: CO-βAla-OH
R$_3$: H

X: O
Y: CH$_3$

SYNTHESIS PATH

N$^α$-9-Fmoc-L-phenylalanyl-rac-α-methoxy-glycinmethylester (LB.6.2)

Empirical Formula (C$_{27}$H$_{28}$N$_2$O$_6$)

Similarly to (PA.1.3), (LB.6.2) was sysnthesized by acid-catalysed reaction from (LB.2.4) in methanol. Yield: (95% of theoretical).— $^1$H-NMR (400 MHz, CDCl$_3$):δ=7.81 (d, 2H, fluorenyl-H$^1$, $^3J_{H,H}$=7.30 Hz), 7.67 (d, 2H, fluorenyl-H$^4$, $^3J_{H,H}$=7.26 Hz), 7.40–7.15 (m, 9H, fluorenyl-H/phenyl-H), 6.1 (d, 1H, NH), 5.47 (d, 1H, NH—CH—OH), 4.40–4.27 (m, 3H, NH—CH—CO/CH—CH$_2$), 4.23 (t, 1H, CH—CH2, $^3J_{H,H}$=6.67 Hz), 3.81 (s, 3H, CH$_3$), 3.42 (s, 3H, CH$_3$), 3.10 (AB-q, 1 H, CH$_2$—C$_6$H$_5$, $^3J_{H,H}$=6.7 Hz, $^2J_{H,H}$=14.0 Hz), 2.95 (AB-q, 1 H, CH$_2$—C$_6$H$_5$, $^3J_{H,H}$=6.7 Hz, $^2J_{H,H}$=14.0 Hz).— $^{13}$C-NMR (75 MHz, CDCl$_3$): δ=174.4 (s, COOH), 172.1 (s, CO—NH$_2$), 156.4 (s, NH—COO), 143.7 (s, fluorenyl-C$_6$), 141.4 (s, fluorenyl-C$_5$), 137.2 (s, phenyl-H), 130.0–120.5 (5 signals) (d, fluorenyl-H/phenyl-H), 72.1 (d, NH—CHOH), 68.1 (t, CH—CH$_2$), 56.6/55.4$^{[dia]}$ (d, NH—CH—CO), 53,0/52.4 (q, CH$_3$), 47.3 (d, CH—CH$_2$), 37.9 (t, CH$_2$—C$_6$H$_5$).— MS (FAB, thioglycerin): m/z=477 (17, [M+H]$^⊕$).

N$^α$-9-Fmoc-L-phenylalanyl-α-methoxy-glycine (LB.6.3) $_{(AB)}$

Empirical Formula (C$_{20}$H$_{21}$N$_2$O$_6$)

Similarly to (LA.2.4), the carboxylic function of (LB.6.2) was released in acetone/water with catalysis by LiOH.— Yield: (62% of theoretical).— 1H-NMR (400 MHz, CDCl$_3$): δ=7.81 (d, 2H, fluorenyl-H$^1$, $^3J_{H,H}$=7.30 Hz), 7.67 (d, 2H, fluorenyl-H$^4$, $^3J_{H,H}$==7.26 Hz), 7.40–7.15 (m, 9H, fluorenyl-H/phenyl-H), 6.1 (d, 1H, NH), 5.47 (d, 1H, NH—CH—OH), 4.40–4.27 (m, 3H, NH—CH—CO/CH—CH$_2$), 4.23 (t, 1H, CH—CH$_2$, $^3J_{H,H}$=6.67 Hz), 3.81 (s, 3H, CH$_3$), 3.42 (s, 3H,CH$_3$), 3.10 (AB-q, 1H, CH$_2$—C$_6$H$_5$, $^3J_{H,H}$=6.7 Hz, J$_{H,H}$=14.0 Hz), 2.95 (AB-q,1H, CH$_2$—C$_6$H$_5$), $^3J_{H,H}$=6.7 Hz,2 J$_{H,H}$=14.0 Hz).— $^{13}$C-NMR (75 MHz, CDCl$_3$): δ=174.4 (s, COOH), 172.1 (s, CO—NH$_2$), 156.4 (s, NH—COO), 143.7 (s, fluorenyl-C$_6$), 141.4 (s, fluorenyl-C$_5$), 137.2 (s, phenyl-H), 130.0–120.5 (5 signals) (d, fluorenyl-H/phenyl-H), 72.1 (d, NH—CHOH), 68.1 (t, CH—CH$_2$), 56.6/55.4$^{[dia]}$ (d, NH—CH—CO), 53,0 (q, CH$_3$), 47.3 (d, CH—CH$_2$), 37.9 (t, CH$_2$—C$_6$H$_5$).— MS (FAB, thioglycerin): m/z=385 (10, [M+H]$^⊕$).

SYNTHESIS PATH A/SYNTHESIS PATH B/ EXAMPLE 7

Transfer to Routine Peptide Synthesis

In addition to the experiments in solution and the synthesis of the model compounds illustrated above, there were built up with the linker blocks (LA.6.1), (LA.7.2) and (LB.3.2) peptides of different sequence (sequence length up to 10 amino acid residues), using an amino-functionalized poly-ethylene glycol resin (TentaGel™ S Amine) or on β-alanin-functionalized cellulose paper (Whatman 3MM) and, when (LB.3.2) is used with 95% TFA/2.5% TIBS/2.5% water, and when (LA.6.1) (LA.7.2) and are used, deprotected in the two-stages processes described above. The polymer materials are thereupon washed, each three times for 10 min. with MeOH/water 1:1 (0.1% HCl) and 1 M acetic acid/water, and dried in HV 12 h. Division of the peptidamides is effected in buffer system (b) (see below) at 50° C. and leads to peptidamides with the expected purity. The results clearly show, that the N.O/N.S-acetal used, and correspondingly protected, as a protective group or anchor group, is stable (Fmoc SPPS) under the basic reaction conditions (e.g. 20% piperidine in DMF) of synthesis of $R_1$.

that the N.O-acetal used, and correspondingly protected, as an anchor group, is stable (Boc SPPS) under the acidic reaction conditions (e,g, 55% TFA/DCM) of the synthesis of $R_1$.

That the deprotected N.O/N.S-acetal is stable under the acidic aqueous conditions, and the correspondingly protected compounds can be purified.

that a division of the protective group (with deprotected hydroxyl or thiol function) is possible under neutral reaction conditions (pH=7).

that the concept can be used both as a protective group and as an anchor group.

Buffers Used
(a) $NaH_2PO_4/Na_2HPO_4/0.1M/pH\ 7.0/H_2O$
(b) $NaH_2PO_4/Na_2HPO_4/0.1M/pH\ 7.5/H_2O$
(c) $NaH_2PO_4/Na_2HPO_4/0.01M/pH\ 7.0/H_2O$
(d) $NaH_2PO_4/Na_2HPO_4/0-01\ M/pH\ 7.5/H_2O$
(e) tris-hydroxymethylaminomethane-hydrochloride (Tris.HCl/0.01 M/pH 7.6/$H_2O$
(f) tris-hydroxymethylaminomethanehydrochloride (Tris.HCl)/0.01 M/pH 8.0/$H_2O$
(g) triethylammonium acetate (TEAAc)/0.01 M/pH 7.0/$H_2O$ Abbreviations Used Amino acid derivates derivate according to IUPAC-IUB [J. Biol. Chem. 260, 14(1983)]

| | |
|---|---|
| Boc | tert.-butyloxycarbonyl |
| tBu | tert-butyl |
| DCHA | dicyclohecylammonium |
| DCM | dichloromethane |
| DIC | N,N'-diisopropylcarbodiimide |
| DMF | dimethylformamide |
| DMSO | dimethylsulfoxide |
| Et | ethyl |
| FAB-MS | "Fast Atom Bombardement" Mass Spectroscopy |
| Fmoc | 9-fluorenyl methoxycarbonyl |
| Hal | halogen |
| HOBt | N-hydroxybenzotriazole |
| HPLC | high-pressure liquid chromatography |
| HV | high vacuum |
| Me | methyl |
| MeIm | N-methylimidazole |
| MOM | methoxymethyl |
| ms | mass spectroscopy |
| MSNT | mesitylenesulfonyl-3-nitro-1.2.4-triazole |
| 3-NBA | 3-nitrobenzylalcohol |
| NMR | nuclear magnetic resonance spectroscopy |
| SEM | trimethylsilylethoxymethyl |
| TBDMS | t-butyl-dimethylsilyl |
| TIBS | triisobutylsilane |
| TFA | trifluoroacetic acid |
| Trt | trityl |

We claim:

1. A process for the preparation of a carbamide formula

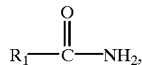

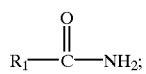 (II)

said process comprising:

a) selecting an organic carboxylic acid having the formula $R_1COOH$ wherein $R^1$ is an organic residue of said organic carboxylic acid;

b) reacting said organic carboxylic acid with a compound of the formula

wherein X is —O— or —S— and Y is a protective group for X, wherein $R_2$ and $R_3$ are identical or different substituents selected from the group consisting of hydrogen and electron withdrawing groups according to the Erlenmeyer rule for O.O, N.O, and N.S. acetals, and wherein $R_2$ and $R_3$ may not both be H, to form a protected carbamide having the formula (I)

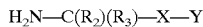

wherein X, Y, $R_1$, $R_2$, and $R_3$ are as defined above, c) reacting said protected carbamide (I) at a first pH whereby the protective group Y is split off; and d) reacting the product formed in step c) at a second pH in a range of 5 to 9 to liberate a carbamide having the wherein the splitting off of said protective group Y in step (c) does not take place at said second pH.

2. The process of claim 1, wherein at least one of $R_2$ and $R_3$ is a haloalkyl group or an optionally derivatized carboxyl group.

3. The process of claim 2, wherein said optionally derivatized carboxyl group is a CO-β-ala-OH group or an alkyl-esterified carboxylic group.

4. The process of claim 1, wherein at least one of $R_2$ and $R_3$ has an additional reactive functionality suitable for creating a link with a carrier material.

5. The process of claim 4, wherein said additional reactive functionality comprises a carboxyl group, an amino group, or a thiol group.

6. The process of claim 1, wherein $R_2$ and $R_3$ are each $CF_3$, and Y is $CH_3$.

7. The process of claim 1, wherein $R_2$ and $R_3$ are each $CF_3$, and wherein Y is an alkyl group other than a methyl group, or is a substituted alkyl group, an aryl group, or an alkylsilyl group.

8. The process of claim 7, wherein Y is selected from the group consisting of ethyl, i-propyl, t-butyl, $CH_2$—O—$CH_3$, $CH_2$—O—$CH_2$—$Si(CH_3)_3$, and t-butyldimethylsilyl.

9. The process of claim 1, wherein prior to step (c), the protected carbamide (I) is employed in a peptide synthesis.

10. The process of claim 9, wherein said peptide synthesis is carried out on a carrier material.

11. The process of claim 1, wherein said protected carbamide (I) is one having $R_2$, $R_3$, X, and Y in combinations selected from the group consisting of X=O, Y=$CH_3$, $R_2$=$R_3$=

$CF_3$; X=O, Y=C($CH_3$)$_3$, $R_2$=H, $R_3$=CO-β-ala-OH; X=O, Y=$CH_2$—O—$CH_3$, $R_2$=$CF_3$, $R_3$=CO-β-ala-OH; X=O, Y=$CH_2$—O—$CH_3$, $R_2$=H, $R_3$=CO-β-ala-OH; X=O, Y=Si($CH_3$)$_2$—C($CH_3$)$_3$, $R_2$=H, $R_3$=CO-β-ala-OH; X=S, Y=$C_2H_5$, $R_2$=H, $R_3$=CO-β-ala-OH; X=S, Y=CH($CH_3$)$_2$, $R_2$=H, $R_3$=CO-β-ala-OH; X=S, Y=C($CH_3$)$_3$, $R_2$=H, $R_3$=CO-β-ala-OH; X=O, Y=$CH_3$, $R_2$=H, $R_3$=C(O)O$CH_3$; X=S, Y=aryl, $R_2$=H, $R_3$=CO-β-ala-OH; and X=S, Y=alkyl, $R_2$=H, $R_3$=CO-β-ala-OH.

12. The process of claim 1, wherein said second pH is about 7.

13. The process of claim 1, wherein $R_1$COOH is the C-terminal end of an amino acid or a peptide.

14. A process for the preparation of a carbamide

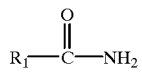

by means of a protected carbamide having the formula

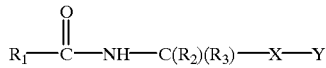 (I)

wherein $R_1$ is an organic residue of an organic carboxylic acid, $R_2$ and $R_3$ are identical or different substituents selected from the group consisting of hydrogen and electron withdrawing groups according to the Erlenmeyer rule for O.O, N.O, and N.S acetals, and wherein $R_2$ and $R_3$ are not both H, X is —O— or —S—, and Y is a protective group, said process comprising:

a) reacting a compound of the formula

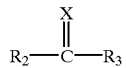

with

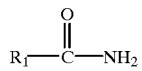

to form a protected carbamide precursor

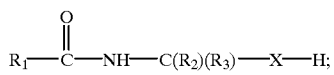 (II)

wherein X, $R_1$, $R_2$ and $R_3$ are defined as above, b) reacting said protected carbamide precursor (II) with a compound reactive with the —X—H moiety of (II), said compound bearing a residue Y, to form said protected carbamide (I);

c) splitting off the protective group Y from said protected carbamide (I) at a first pH to reform (II); and d) at a second pH within the range of 5 to 9, decomposing (II) to release

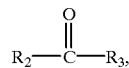

and yield the carbamide

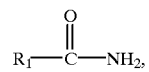

wherein the step (d) of decomposing (II) does not take place at said first pH which is used in step (c).

15. The process of claim 14, wherein at least one of $R_2$ and $R_3$ is a haloalkyl group or an optionally derivatized carboxyl group.

16. The process of claim 15, wherein said optionally derivatized carboxyl group is a CO-β-ala-OH group or an alkyl-esterified carboxylic group.

17. The process of claim 14, wherein at least one of $R_2$ and $R_3$ has an additional reactive functionality suitable for creating a link with a carrier material.

18. The process of claim 17, wherein said additional reactive functionality comprises a carboxyl group, an amino group, or a thiol group.

19. The process of claim 14, wherein $R_2$ and $R_3$ are each $CF_3$, and Y is $CH_3$.

20. The process of claim 14, wherein $R_2$ and $R_3$ are each $CF_3$, and wherein Y is an alkyl group other than a methyl group, or is a substituted alkyl group, an aryl group, or an alkylsilyl group.

21. The process of claim 20, wherein Y is selected from the group consisting of ethyl, i-propyl, t-butyl, $CH_2$—O—$CH_3$, $CH_2$—O—$CH_2$—Si($CH_3$)$_3$, and t-butyldimethylsilyl.

22. The process of claim 14, wherein prior to step (c), the protected carbamide (I) is employed in a peptide synthesis.

23. The process of claim 22, wherein said peptide synthesis is carried out on a carrier material.

24. The process of claim 14, wherein said protected carbamide (I) is one having $R_2$, $R_3$, X, and Y in combinations selected from the group consisting of X=O, Y=$CH_3$, $R_2$=$R_3$=$CF_3$; X=O, Y=C($CH_3$)$_3$, $R_2$=H, $R_3$=CO-β-ala-OH; X=O, Y=$CH_2$—O—$CH_3$, $R_2$=$CF_3$, $R_3$=CO-β-ala-OH; X=O, Y=$CH_2$—O—$CH_3$, $R_2$=H, $R_3$=CO-β-ala-OH; X=O, Y=Si($CH_3$)$_2$—C($CH_3$)$_3$, $R_2$=H, $R_3$=CO-β-ala-OH; X=S, Y=$C_2H_5$, $R_2$=H, $R_3$=CO-β-ala-OH; X=S, Y=CH($CH_3$)$_2$, $R_2$=H, $R_3$=CO-β-ala-OH; X=S, Y=C($CH_3$)$_3$, $R_2$=H, $R_3$=CO-β-ala-OH; X=O, Y =$CH_3$, $R_2$=H, $R_3$=C(O)O$CH_3$; X=S, Y=aryl, $R_2$=H, $R_3$=CO-β-ala-OH; and X=S, Y=alkyl, $R_2$=H, $R_3$=CO-β-ala-OH.

25. The process of claim 14, wherein said second pH is about 7.

26. The process of claim 14, wherein

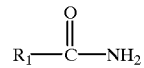

is the amide of the C-terminal end of an amino acid or peptide.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH:  5 Amino Acids
        (B) TYPE:  Amino Acids
        (D) TOPOLOGY: Not Relevant (ii) MOLECULE TYPE:  Peptide (ix) FEATURE:
        (A) NAME/KEY: Protective or anchor group-
            containing peptide
        (D) OTHER INFORMATION:  First Xaa is
            t-butyloxycarbonyl lysine, second Xaa
            is '-rac-t-butoxy-Gly, Ala is bAla-OH (xi) SEQUENCE DESCRIPTION:  SEQ ID NO: 1:

Xaa Phe Phe Xaa Ala
1               5

(2) INFORMATION FOR SEQ ID NO:2:

(i) SEQUENCE CHARACTERISTICS:
        (A) LENGTH:  5 Amino Acids
        (B) TYPE:  Amino Acids
        (D) TOPOLOGY: Not Relevant (ii) MOLECULE TYPE:  Peptide (ix) FEATURE:
        (A) NAME/KEY: Protective or anchor group-
            containing peptide
        (D) OTHER INFORMATION:  First Xaa is
            t-butyloxycarbonyl lysine, first Ala is '-rac-methoxymethyl Ala, second Ala is
bAla-OH (xi) SEQUENCE DESCRIPTION: SEQ ID NO: 2:

Xaa Phe Phe Ala Ala
1               5

(2) INFORMATION FOR SEQ ID NO:3:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, first Ala is
            '-rac-methoxy- -trifluoromethyl Ala,
            second Ala is bAla (xi) SEQUENCE DESCRIPTION: SEQ ID NO: 3:

Xaa Phe Phe Ala Ala
1               5

(2) INFORMATION FOR SEQ ID NO:4:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is '-(alkoxymethyl)-oxy-Gly, Ala is
            bAla (xi) SEQUENCE DESCRIPTION: SEQ ID NO: 4:

Xaa Phe Phe Xaa Ala
1               5

(2) INFORMATION FOR SEQ ID NO:5:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is '-rac-tert-butyl-dimethylsiloxy-Gly,
            Ala is bAla (xi) SEQUENCE DESCRIPTION: SEQ ID NO: 5:

Xaa Phe Phe Xaa Ala
1               5

(2) INFORMATION FOR SEQ ID NO:6:

```
      (i) SEQUENCE CHARACTERISTICS:
          (A) LENGTH:  5 Amino Acids
          (B) TYPE:  Amino Acids
          (D) TOPOLOGY: Not Relevant (ii) MOLECULE TYPE:  Peptide (ix) FEATURE:
          (A) NAME/KEY: Protective or anchor group-
              containing peptide
          (D) OTHER INFORMATION:  First Xaa is
              t-butyloxycarbonyl lysine, second Xaa
              is '-rac-tert-butyl-dimethylsiloxy-Gly,
              Ala is bAla-OH (xi) SEQUENCE DESCRIPTION: SEQ ID NO: 6:

Xaa Phe Phe Xaa Ala
1               5

(2) INFORMATION FOR SEQ ID NO:7:

(i) SEQUENCE CHARACTERISTICS:
          (A) LENGTH:  5 Amino Acids
          (B) TYPE:  Amino Acids
          (D) TOPOLOGY: Not Relevant (ii) MOLECULE TYPE:  Peptide (ix) FEATURE:
          (A) NAME/KEY: Protective or anchor group-
              containing peptide
          (D) OTHER INFORMATION:  First Xaa is
              t-butyloxycarbonyl lysine, second Xaa
              is '-rac-ethylthio-Gly, Ala is bAla-OH (xi) SEQUENCE DESCRIPTION: SEQ ID NO: 7:

Xaa Phe Phe Xaa Ala
1               5

(2) INFORMATION FOR SEQ ID NO:8:

(i) SEQUENCE CHARACTERISTICS:
          (A) LENGTH:  5 Amino Acids
          (B) TYPE:  Amino Acids
          (D) TOPOLOGY: Not Relevant (ii) MOLECULE TYPE:  Peptide (ix) FEATURE:
          (A) NAME/KEY: Protective or anchor group-
              containing peptide
          (D) OTHER INFORMATION:  First Xaa is
              t-butyloxycarbonyl lysine, second Xaa
              is '-rac-isopropylthio-Gly, Ala is
              bAla-OH (xi) SEQUENCE DESCRIPTION: SEQ ID NO: 8:

Xaa Phe Phe Xaa Ala
1               5

(2) INFORMATION FOR SEQ ID NO:9:

(i) SEQUENCE CHARACTERISTICS:
          (A) LENGTH:  5 Amino Acids
          (B) TYPE:  Amino Acids
          (D) TOPOLOGY: Not Relevant (ii) MOLECULE TYPE:  Peptide (ix) FEATURE:
          (A) NAME/KEY: Protective or anchor group-
              containing peptide
          (D) OTHER INFORMATION:  First Xaa is
              t-butyloxycarbonyl lysine, second Xaa
``` is '-rac-tert-butylthio-Gly, Ala is
bAla-OH (xi) SEQUENCE DESCRIPTION: SEQ ID NO: 9:

Xaa Phe Phe Xaa Ala
1               5

(2) INFORMATION FOR SEQ ID NO:10:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is '-rac-tert-butylthio-Gly, Ala is
            bAla (xi) SEQUENCE DESCRIPTION: SEQ ID NO: 10:

Xaa Phe Phe Xaa Ala
1               5

(2) INFORMATION FOR SEQ ID NO:11:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is '-rac-tert-butylthio-Gly, Ala is
            bAla linked at carboxy terminus to
            TentaGel S-amine (amino-functional
            glycol-styrol graft polymer)

(xi) SEQUENCE DESCRIPTION: SEQ ID NO: 11:

Xaa Phe Phe Xaa Ala
1               5

(2) INFORMATION FOR SEQ ID NO:12:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is '-rac-alkyl/arylthiol-Gly, Ala is
            bAla-OH (xi) SEQUENCE DESCRIPTION: SEQ ID NO: 12:

Xaa Phe Phe Xaa Ala
1               5

(2) INFORMATION FOR SEQ ID NO:13:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is '-rac-(methoxymethyl)oxy-Gly, Ala is
            bAla-OH (xi) SEQUENCE DESCRIPTION: SEQ ID NO: 13:

Xaa Phe Phe Xaa Ala
1               5

(2) INFORMATION FOR SEQ ID NO:14:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is (trimethylsiloxyethyl)oxy-Gly, Ala
            is bAla-OH (xi) SEQUENCE DESCRIPTION: SEQ ID NO: 14:

Xaa Phe Phe Xaa Ala
1               5

(2) INFORMATION FOR SEQ ID NO:15:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is tert-butoxycarbonyl (boc) Trp, third
            Xaa is tert-butyl Asp, fourth Xaa is
            trityl-Asn, fifth Xaa is Phe-NH2

(xi) SEQUENCE DESCRIPTION: SEQ ID NO: 15:

Xaa Xaa Xaa Xaa Xaa
1               5

(2) INFORMATION FOR SEQ ID NO:16:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:

(A) NAME/KEY: Protective or anchor group-
            containing peptide
        (D) OTHER INFORMATION: First Xaa is
            t-butyloxycarbonyl lysine, second Xaa
            is '-rac-tert-butoxy-Gly, Ala is bAla (xi) SEQUENCE DESCRIPTION: SEQ ID NO: 16:

Xaa Phe Phe Xaa Ala
1               5

(2) INFORMATION FOR SEQ ID NO:17:

(i) SEQUENCE CHARACTERISTICS:
        (A) LENGTH: 5 Amino Acids
        (B) TYPE: Amino Acids
        (D) TOPOLOGY: Not Relevant (ii) MOLECULE TYPE: Peptide (ix) FEATURE:
        (A) NAME/KEY: Protective or anchor group-
            containing peptide
        (D) OTHER INFORMATION: First Xaa is
            t-butyloxycarbonyl lysine, second Xaa
            is '-rac-methoxy-Gly, Ala is bAla-OH (xi) SEQUENCE DESCRIPTION: SEQ ID NO: 17:

Xaa Phe Phe Xaa Ala
1               5